US008551741B2

(12) United States Patent
Usuda et al.

(10) Patent No.: US 8,551,741 B2
(45) Date of Patent: Oct. 8, 2013

(54) METHOD FOR PRODUCING AN L-AMINO ACID

(75) Inventors: Yoshihiro Usuda, Kawasaki (JP);
Seizaburo Shiraga, Kawasaki (JP);
Kazuhiko Matsui, Kawasaki (JP);
Shigeo Suzuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 127 days.

(21) Appl. No.: 12/479,010

(22) Filed: Jun. 5, 2009

(65) Prior Publication Data
US 2009/0291478 A1 Nov. 26, 2009

Related U.S. Application Data

(63) Continuation of application No. PCT/JP2007/074194, filed on Dec. 11, 2007.

(60) Provisional application No. 60/871,842, filed on Dec. 26, 2006.

(30) Foreign Application Priority Data

Dec. 11, 2006 (JP) ................................. 2006-333604

(51) Int. Cl.
*C12P 13/04* (2006.01)

(52) U.S. Cl.
USPC ........... 435/106; 435/112; 435/113; 435/115; 435/41

(58) Field of Classification Search
None
See application file for complete search history.

(56) References Cited

U.S. PATENT DOCUMENTS

| | | | |
|---|---|---|---|
| 4,485,173 A * | 11/1984 | Gierhart ........................ 435/134 |
| 5,175,107 A | 12/1992 | Debabov et al. | |
| 5,567,606 A | 10/1996 | Hayashi et al. | |
| 5,661,012 A | 8/1997 | Sano et al. | |
| 5,688,671 A | 11/1997 | Sugimoto et al. | |
| 5,827,698 A | 10/1998 | Kikuchi et al. | |
| 5,830,716 A | 11/1998 | Kojima et al. | |
| 5,932,453 A | 8/1999 | Kikuchi et al. | |
| 6,040,160 A | 3/2000 | Kojima et al. | |
| 6,132,999 A | 10/2000 | Debabov et al. | |
| 6,303,348 B1 | 10/2001 | Livshits et al. | |
| 6,319,696 B1 | 11/2001 | Kishino et al. | |
| 6,911,332 B2 | 6/2005 | Usuda et al. | |
| 7,026,149 B2 | 4/2006 | Usuda et al. | |
| 7,029,893 B2 | 4/2006 | Usuda et al. | |
| 7,060,475 B2 | 6/2006 | Usuda et al. | |
| 7,090,998 B2 | 8/2006 | Ishikawa et al. | |
| 7,186,531 B2 | 3/2007 | Akhverdian et al. | |
| 7,192,748 B2 | 3/2007 | Usuda et al. | |
| 7,211,415 B2 * | 5/2007 | Rieping et al. ................ 435/106 |
| 7,220,570 B2 | 5/2007 | Usuda et al. | |
| 7,306,933 B2 | 12/2007 | Van Dien et al. | |
| 7,468,262 B2 | 12/2008 | Usuda et al. | |
| 2002/0110876 A1 | 8/2002 | Miyata et al. | |
| 2002/0155556 A1 | 10/2002 | Imaizumi et al. | |
| 2002/0160461 A1 | 10/2002 | Nakai et al. | |
| 2004/0132165 A1 | 7/2004 | Akhverdian et al. | |
| 2004/0265956 A1 | 12/2004 | Takikawa et al. | |
| 2005/0233308 A1 | 10/2005 | Nishio et al. | |
| 2005/0239177 A1 | 10/2005 | Livshits et al. | |
| 2006/0019355 A1 | 1/2006 | Ueda et al. | |
| 2006/0088919 A1 | 4/2006 | Rybak et al. | |
| 2006/0216796 A1 | 9/2006 | Hashiguchi et al. | |
| 2006/0234356 A1 | 10/2006 | Usuda et al. | |
| 2006/0234357 A1 | 10/2006 | Usuda et al. | |
| 2006/0257979 A1 * | 11/2006 | Dusch .......................... 435/106 |
| 2007/0004014 A1 | 1/2007 | Tsuji et al. | |
| 2007/0249017 A1 | 10/2007 | Usuda et al. | |
| 2009/0068712 A1 | 3/2009 | Terashita et al. | |
| 2009/0093029 A1 | 4/2009 | Usuda et al. | |
| 2009/0104659 A1 | 4/2009 | Smirnov et al. | |

FOREIGN PATENT DOCUMENTS

| | | |
|---|---|---|
| JP | 11-243956 | 9/1999 |
| WO | WO01/53459 | 7/2001 |
| WO | WO2008/072761 | 6/2008 |

OTHER PUBLICATIONS

Salanitro and Wegener, 1971. Growth of *Escherichia coli* on short-chain fatty acids: Growth characteristics of mutants. Journal of Bacteriology, vol. 108(2):885-892.*

Ansel et al, 1999. Pharmaceutical Dosage Forms and Drug Delivery Systems. Chapter 13. Disperse Systems. Emulsion Section. pp. 364-375.*

Maloy et al., The Journal of Biological Chemistry, 1981, vol. 256, No. 8, p. 3735-3742.*

Kramer, R., Journal of Bacteriology, 1996, vol. 45, p. 1-21.*

Campbell et al., Molecular Microbiology, 2003, vol. 47, No. 3., p. 793-805.*

Vorum, H., et al., "Solubility of long-chain fatty acids in phosphate buffer at pH 7.4," Biochimica et Biophysica Acta 1992;1126:135-142.

Weeks, G., et al., "Control of Fatty Acid Metabolism 1. Induction of the Enzymes of Fatty Acid Oxidation in *Escherichia coli*," J. Bacteriol. 1969;97(2):827-836.

U.S. Appl. No. 11/877,726, filed Oct. 24, 2007, Van Dien et al.
U.S. Appl. No. 12/055,438, filed Mar. 26, 2008, Iwatani et al.
U.S. Appl. No. 12/354,042, filed Jan. 15, 2009, Ptitsyn et al.
U.S. Appl. No. 12/420,934, filed Apr. 9, 2009, Tajima et al.

(Continued)

*Primary Examiner* — Kade Ariani

(74) *Attorney, Agent, or Firm* — Shelly Guest Cermak; Cermak Nakajima LLP

(57) ABSTRACT

An L-amino acid is produced by culturing a bacterium of the Enterobacteriaceae family which has an L-amino acid-producing ability in a medium containing fatty acids as the carbon source, particularly fatty acids which have been subjected to emulsification or homogenization, to thereby produce and accumulate the L-amino acid in a culture medium; and collecting the L-amino acid from the culture medium.

11 Claims, No Drawings

(56) References Cited

OTHER PUBLICATIONS

Ren, Y., et al., "An Alternative Pathway of Oleate β-Oxidation in *Escherischia coli* Involving the Hydrolysis of a Dead End Intermediate by a Thioesterase," J. Biol. Chem. 2004;279(12):11042-11050.

Salanitro, J. P., et al., "Growth of *Escherischia coli* on Short-Chain Fatty Acids: Growth Characteristics of Mutants," J. Bacteriol. 1971;108(2):885-892.

* cited by examiner

METHOD FOR PRODUCING AN L-AMINO ACID

This application is a continuation under 37 C.F.R. §120 of PCT/JP2007/074194, filed Dec. 11, 2007, which claims priority under 35 U.S.C. §119 to Japanese Patent Application No. 2006-333604, filed on Dec. 11, 2006, and U.S. Provisional Patent Application No. 60/871,842, filed Dec. 26, 2006, all of which are incorporated in their entireties by reference. The Sequence Listing in electronic format filed herewith is also hereby incorporated by reference in its entirety (File Name: US-353_Seq_List; File Size: 33 KB; Date Created: Jun. 5, 2009).

BACKGROUND OF THE INVENTION

1. Field of the Invention

The present invention relates to a method for producing L-amino acids using bacteria. L-amino acids have many useful and various applications, including as additives in seasonings, food additives, feed additives, chemical products, and drugs.

2. Brief Description of the Related Art

L-amino acids such as L-threonine and L-lysine are industrially produced by fermentation methods using L-amino acid-producing bacteria such as *Escherichia* bacteria. Examples of L-amino acid-producing bacteria can include bacterial strains isolated from nature or artificially mutated strains, as well as recombinant strains obtained by modifying the bacteria so that the activities of L-amino acid biosynthetic enzymes are enhanced. Methods for producing L-threonine can include those disclosed in JP 05-304969 A, WO 98/04715, JP 05-227977 A, and US 2002/0110876 A. Methods of producing L-lysine include those disclosed in JP 10-165180 A, JP 11-192088 A, JP 2000-253879 A, and JP 2001-057896 A.

In fermentative production of an L-amino acid, sugars such as glucose, fructose, sucrose, molasses, and starch hydrolysate are generally used as sources of carbon.

Clark et al. reported that an *Escherichia coli* wild-type strain can grow in a medium containing long-chain fatty acids (12 or more carbon atoms) as the sole carbon source (Clark, D. P. and Cronan Jr., J. E. 1996. p. 2343-2357. In F. D. Neidhardt (ed.), *Escherichia coli* and *Salmonella* Cellular and Molecular Biology/Second Edition, American Society for Microbiology Press, Washington, D.C.). Weeks et al. reported that an *Escherichia coli* wild-type strain can grow in a medium containing palmitic acid or oleic acid as the sole carbon source (Weeks, G., Shapiro, M. Burns, R. O., and Wakil, S. J. 1969. Control of Fatty Acid Metabolism I. Induction of the Enzymes of Fatty Acid Oxidation in *Escherichia coli*. J. Bacteriol. 97:827-836). However, the solubility of fatty acids is known to be extremely low, and Vorum et al. reported that the solubility of oleic acid is 0.0003 g/l or less, and that of palmitic acid is 0.00000003 g/l or less, whereas the solubility of lauric acid is 0.1 g/l or more (Vorum, H., Brodersen, R., Kragh-Hansen, U., and Pedersen, A. O, Solubility of long-chain fatty acids in phosphate buffer at pH 7.4. 1992. Biochimica et Biophysica Acta, Lipids and Lipid Metabolism 1126: 135-142).

Therefore, there are very few examples of production of substances by a direct fermentation method using fatty acids as the sole carbon source, and there have been no reports of production of an L-amino acid by such methods. Furthermore, when fatty acids are employed as the sole carbon source, the concentration of the fatty acids is typically about 1 g/l. For example, JP 11-243956 A discloses an example of production of polyester, where the culture medium contains only 2 g/l lauric acid as the carbon source.

SUMMARY OF THE INVENTION

The present invention provides a method for producing an L-amino acid by fermentation without utilizing sugar as the carbon source. Such a method can be performed at lower cost by using a fermentative material in accordance with the presently disclosed subject matter.

In accordance with the presently disclosed subject matter the inventors have made intensive studies to solve the above-mentioned problems. As a result, they have found that an L-amino acid can be produced by culturing a bacterium of Enterobacteriaceae family having an L-amino acid-producing ability in a medium containing a fatty acid as the carbon source. Previously, fatty acids were not considered to be useful in fermentation due to their extremely low solubility in water. Moreover, it has been found that L-amino acid production can be enhanced when the fatty acids in the medium have been subject to emulsification or homogenization.

An aspect of the present invention is to provide a method for producing an L-amino acid, comprising culturing a bacterium of the Enterobacteriaceae family having an L-amino acid-producing ability in a medium containing a fatty acid, and collecting the L-amino acid from the medium or bacterium.

Another aspect of the present invention is to provide the method as described above, wherein said fatty acid comprises a fatty acid having no less than 14 carbons.

Another aspect of the present invention is to provide the method as described above, wherein said fatty acid is selected from the group consisting of myristic acid, palmitic acid, stearic acid, oleic acid, linoleic acid, and combinations thereof.

Another aspect of the present invention is to provide the method as described above, wherein said medium comprises said fatty acid in an amount of 0.2 to 10 w/v %.

Another aspect of the present invention is to provide the method as described above, wherein said medium further comprises a carbon source other than a fatty acid.

Another aspect of the present invention is to provide the method as described above, wherein said fatty acid is emulsified.

Another aspect of the present invention is to provide the method as described above, wherein said emulsification occurs by a method selected from the group consisting of adding a surfactant to said medium, homogenization, ultrasonication, and combinations thereof.

Another aspect of the present invention is to provide the method as described above, wherein said emulsification occurs by homogenization and/or ultrasonication in the presence of a surfactant under alkali conditions.

Another aspect of the present invention is to provide the method as described above, wherein said bacterium belongs to the genus *Escherichia*.

Another aspect of the present invention is to provide the method as described above, wherein said L-amino acid is selected from the group consisting of L-threonine, L-lysine, L-phenylalanine, L-tryptophan, L-valine, L-leucine, L-isoleucine, L-methionine, and combinations thereof.

Another aspect of the present invention is to provide the method as described above, wherein the L-amino acid is selected from the group consisting of L-threonine, L-lysine, and combinations thereof.

DETAILED DESCRIPTION OF EXEMPLARY EMBODIMENTS

Hereinafter, the present invention will be described in detail.

<1> Method of the Present Invention

The method for producing an L-amino acid in accordance with the presently disclosed subject matter can include the steps of culturing a bacterium of the Enterobacteriaceae family having an L-amino acid-producing ability in a medium containing a fatty acid to cause accumulation of the L-amino acid in the medium or bacterial cells; and collecting the L-amino acid from the medium or bacterial cells. The method can employ a batch culture, fed-batch culture, or continuous culture, and the fatty acids can be present in the starting medium, the feed medium, or both.

A fed-batch culture can be when a medium is continuously or intermittently added to the culture container, and medium is not removed from the container until the culture is complete. A continuous culture can be when a medium is continuously or intermittently added to the culture container, and medium is then removed from the container, in general, in an amount equal to the amount of the medium added. The starting medium can be a medium used in the batch culture before adding the feed medium in the fed-batch culture or continuous culture, for example, the medium used at the start of the culture. The feed medium can be a medium which is added to the fermenter in the fed-batch culture or continuous culture. Moreover, a batch culture can be a method which includes inoculating a strain into fresh medium prepared per batch, where the medium is not added until the bacterial cells are collected.

Fatty acids are monovalent carboxylic acids having a long hydrocarbon chain which is designated as $C_nH_m$COOH (n+1 and m+1 represent carbon number and hydrogen number contained in the fatty acid, respectively). Generally, fatty acids with 12 or more carbons are considered long chain fatty acids. There are many kinds of fatty acids having different numbers of carbons and different degrees of unsaturation. It is also known that fatty acids are a component of oil, and the fatty acid composition is different depending on the kind of oil. Myristic acid ($C_{13}H_{27}$COOH) is a saturated fatty acid having 14 carbon atoms and is present in coconut and palm oils. Palmitic acid ($C_{15}H_{31}$COOH) is a saturated fatty acid having 16 carbon atoms and is present in a large amount in vegetable oil. Stearic acid ($C_{17}H_{35}$COOH) is a saturated fatty acid having 18 carbon atoms and is present in a large amount in animal fat or vegetable oil. Oleic acid ($C_{17}H_{33}$COOH) is a long-chain unsaturated monovalent fatty acid having 18 carbon atoms and is present in a large amount in animal fat or vegetable oil. Linoleic acid ($C_{17}H_{31}$COOH) is a multivalent unsaturated fatty acid having 18 carbon atoms and cis-9,12-double bonds.

Mixtures of long chain fatty acids can be obtained by the hydrolysis of oil. Specifically, mixtures of fatty acids containing palmitic acid, stearic acid, and oleic acid can be obtained by hydrolysis of palm oil. Such fatty acid mixtures can be used in the method of the present invention. Fatty acids which can be extracted from animal oil, vegetable oil, food waste oil, and other oil mixtures, or from fat-containing food such as chocolate can be used. Fatty acids extracted during the purification of oil can also be used.

The concentration of fatty acids in the medium is not particularly limited as long as the chosen bacterium can assimilate the fatty acid as the carbon source, but when fatty acids are added as the sole carbon source to the medium, the concentration can be not more than 10 w/v %, not more than 5 w/v %, or not more than 2 w/v %. Meanwhile, the concentration can be not less than 0.2 w/v %, not less than 0.5 w/v %, or not less than 1.0 w/v %.

When fatty acids are added as the sole carbon source to a fed-batch medium, the concentration of fatty acids in the medium can be not more than 5 w/v %, not more than 2 w/v %, or not more than 1 w/v %. The fatty acid concentration in the fed-batch medium can be controlled to not less than 0.2 w/v %, not less than 0.5 w/v %, or not less than 1.0 w/v %.

The concentration of fatty acids can be determined by gas chromatography (Hashimoto, K., Kawasaki, H., Akazawa, K., Nakamura, J., Asakura, Y., Kudo, T., Sakuradani, E., Shimizu, S., Nakamatsu, T. 1996. Biosci. Biotechnol. Biochem. 70:22-30) or HPLC (Lin, J. T., Snyder, L. R., and McKeon, T. A. 1998. J. Chromatogr. A. 808: 43-49).

In addition, the fatty acids can be in the form of a water-soluble salt with an alkali metal such as sodium or potassium. However, in some instances, the solubility of a sodium or potassium salt of a fatty acid might be insufficient to be used in fermentation. Accordingly, in order for a fatty acid to be efficiently assimilated as the carbon source by a bacterium having an L-amino acid-producing ability, a step can be added which promotes homogenization such as emulsification. For example, emulsification can be achieved by adding an emulsification promoting agent or a surfactant. Emulsification promoting agents can include phospholipids and sterols. Surfactants can include nonionic surfactants such as a polyoxyethylene sorbitan fatty acid ester including poly(oxyethylene) sorbitan monooleate (Tween 80), and an alkyl glucoside including N-octyl β-D-glucoside, and zwitterionic surfactants such as an alkyl betaine including N,N-dimethyl-N-dodecylglycine betaine. General surfactants such as Triton X-100, polyoxyethylene (20) cetyl ether (Brij-58), and nonylphenol ethoxylate (Tergitol NP-40) can also be used.

Moreover, promotion of emulsification or homogenization of a fatty acid also can be effective. Methods for such promotion are not particularly limited as long as promotion of emulsification or homogenization of a fatty acid is obtained. Specific examples thereof can include homogenizer treatment, homomixer treatment, ultrasonication, high pressure treatment, and heat treatment. These treatments can be combined with the above-mentioned surfactant treatments. These treatments can be performed under alkali conditions, such as at a pH 9.0 or more, or at a pH 10 or more.

When mixtures of fatty acids are used as the carbon source, the mixing ratio of fatty acids is not particularly limited as long as the chosen bacterium can assimilate the fatty acids as the carbon source.

The chosen medium can contain a carbon source other than fatty acids. Examples thereof can include sugars such as glucose, fructose, sucrose, lactose, galactose, molasses, starch hydrolysate, and carbohydrate solution obtained by hydrolyzing biomass, alcohols such as ethanol, and organic acids such as fumaric acid, citric acid, and succinic acid. When using a carbon source other than fatty acids, the ratio of fatty acid(s) with respect to the entire source of carbon can be 10 wt % or more, 30 wt % or more, or 50 wt % or more.

Fatty acid(s) can be present in the medium during the entire culture period at a constant concentration, present only in the fed-batch medium, or present only in the starting medium. Also, during periods of the culture, fatty acid(s) can be absent from the medium, as long as the medium contains a sufficient amount of another carbon source during these periods. That is, the time periods wherein the medium contains no fatty acids can be a period of 10%, 20%, or at maximum 30% with respect to the whole fermentation period, for example. In accordance with the presently disclosed subject matter, the phrase "culture in a medium containing fatty acid(s)" can include a culture medium that contains fatty acid(s) for a only a period of the culture, but can lack fatty acids for another period.

The chosen medium additionally can contain other components such as a nitrogen source, an inorganic ion, and if necessary, other organic nutrients.

Examples of a nitrogen source can include ammonia, an ammonium salt such as ammonium sulfate, ammonium carbonate, ammonium chloride, ammonium phosphate, ammonium acetate, urea, and a nitrate salt. Ammonia gas or ammonia water can be used to adjust the pH, and also can be used as a nitrogen source. In addition, peptone, yeast extract, meat extract, malt extract, corn steep liquor, and soybean hydrolysate may also be used. In the medium, these nitrogen sources can be present alone or in combination, and can be present in the starting medium or the feed medium. In addition, both the starting medium and feed medium can contain the same nitrogen source or different nitrogen sources.

The chosen medium can further contain a source of phosphoric acid and/or a sulfate in addition to the above-mentioned components. The phosphoric acid source can be, for example, potassium dihydrogen phosphate, dipotassium hydrogen phosphate, and a phosphate polymer such as pyrophosphoric acid. The sulfate source is not particularly limited as long as it contains a sulfur atom. Sulfate, thiosulfate, or sulfite can be used, as well as a sulfur-containing amino acids such as cysteine, cystine, or glutathione. Ammonium sulfate can be used.

A medium can contain a growth promoter or a nutrient having a growth-promoting effect. Growth promoters can include trace metals, amino acids, vitamins, nucleic acids, peptones, casamino acid, yeast extracts, and soybean hydrolysates containing these. Examples of the trace metals can include iron, manganese, magnesium, and calcium, and examples of the vitamins include vitamin B1, vitamin B2, vitamin B6, nicotinic acid, nicotinamide, and vitamin B 12. These growth promoters can be present in the starting medium, fed-batch medium, or both.

Moreover, when using an auxotrophic mutant that requires an amino acid or the like for its growth, the medium should be supplemented with the required nutrient. In particular, as described below, a large number of L-lysine-producing bacteria have a strong L-lysine biosynthesis pathway and a weak L-lysine degradation ability; therefore, one or more amino acids, such as L-threonine, L-homoserine, L-isoleucine, and L-methionine, can be added to the medium. The compositions of the starting medium and fed-batch medium can be the same or different. Meanwhile, the concentrations of sulfur in the starting medium and fed-batch medium can be the same or different. Moreover, when the feed medium is added in multiple stages, the compositions of the respective feed media can be the same or different.

The culture can be performed with aeration at a fermentation temperature of 20 to 45° C., more preferably 33 to 42° C. The concentration of oxygen can be adjusted within a range of 5 to 50%, or to about 10%. In addition, the culture can be performed with aeration while pH is controlled to 5 to 9. If the pH falls during culture, the medium can be neutralized by adding calcium carbonate or an alkaline such as ammonia gas or ammonia water. When the culture is performed under such conditions for about 10 to 120 hours, a significant amount of L-amino acids accumulate in the culture medium. The concentration of the L-amino acid is not particularly limited, as long as it is sufficient to be collected/recovered from the medium. Exemplary concentrations can be not less than 50 g/L, not less than 75 g/L, or not less than 100 g/L.

The L-amino acid can be collected from the culture medium after completion of culture in accordance with known recovery methods. For example, the L-amino acid can be collected by removing bacterial cells from the culture medium by centrifugation or the like followed by concentration and/or crystallization.

In accordance with the presently disclosed subject matter, in order to keep the accumulation of an L-amino acid at a certain level, the culture of the bacterium can be divided into a seed culture and main culture. The seed culture can be performed with shaking using a flask or the like or batch culture, while the main culture can be performed by fed-batch culture or continuous culture. Alternatively, both of the seed culture and main culture can be performed by batch culture.

When the fed-batch culture or continuous culture is performed in accordance with the presently disclosed subject matter, the feed medium can be added intermittently so that addition of the fatty acid or other carbon source is stopped temporarily. The addition of the feed medium can be stopped for a period of at maximum 30% or less. However, other stopping periods can be specified, such as 20% or less, or 10% or less with respect to the whole period of adding the medium. When the feed medium is added intermittently, the concentration of the substrate in the fermenter can be automatically maintained at a low level throughout the culture by controlling the culture system so that addition of the medium begins when a computer detects an increase in pH or an increase in concentration of dissolved oxygen in the medium due to exhaustion of the carbon source (U.S. Pat. No. 5,912,113 B).

The feed medium for the fed-batch culture can contain a fatty acid, another carbon source, and a nutrient having a growth-promoting effect (growth promoter). The concentration of the fatty acid in the fermentation medium can be controlled to a certain level or less. Herein, the "certain level or less" means that the medium to be added is adjusted so that the fermentation medium contains a fatty acid in an amount of 10 w/v % or less, 5 w/v % or less, or 1 w/v % or less.

Examples of other carbon sources in the feed medium can include glucose, sucrose, and fructose, while examples of the growth promoter in the feed medium can include a nitrogen source, phosphoric acid, and an amino acid. Examples of the nitrogen source in the feed medium can include ammonia, an ammonium salt such as ammonium sulfate, ammonium carbonate, ammonium chloride, ammonium phosphate, ammonium acetate, urea, and a nitrate. Examples of a phosphoric acid source in the feed medium can include potassium dihydrogen phosphate and dipotassium hydrogen phosphate, and when an amino acid-auxotrophic mutant strain is cultured, a required amino acid can be supplemented in the feed medium. The feed medium can be a single medium or a combination of two or more media. When using two or more feed media, these media can be mixed and fed from one feed pipe, or fed from a plurality of feed pipes.

When using a continuous culture method in accordance with the presently disclosed subject matter, the culture medium can be withdrawn at the same time as adding the feed medium, or adding the medium can be performed after a part of the culture medium is withdrawn. In addition, a continuous culture method can be used to reuse bacterial cells, which includes withdrawing the culture medium containing an L-amino acid and cells and returning only the cells to the fermenter (FR 2669935 B). The method of continuously or intermittently adding a nutrient can be the same method as in the fed-batch culture.

The continuous culture method to reuse bacterial cells can include intermittently or continuously withdrawing a fermentation medium when the concentration of an L-amino acid reaches a predetermined level, collecting only the L-amino acid, and recycling the filtration residue containing the bacterial cells in the fermenter, and it can be performed with reference to FR 2669935 B, for example.

Herein, when intermittently withdrawing the culture medium, the L-amino acid can be withdrawn when the concentration of the L-amino acid reaches a predetermined level. Then, fresh medium can be added to a final volume which is preferably the same as the amount of medium before withdrawing the culture medium. Herein, the "same" means a volume of about 93 to 107% of the volume of the culture medium before withdrawing of the medium.

Continuous withdraw of the culture medium can be started simultaneously with or after the addition of the feed medium. When withdrawing the culture medium after the addition of the feed medium, it can be done, for example, within 5 hours, within 3 hours, or within 1 hour after adding the medium. Meanwhile, the volume of the medium which is withdrawn can be the same as that which is added.

<2> Bacterium

In accordance with the presently disclosed subject matter, a bacterium of the Enterobacteriaceae family can be used which has an L-amino acid-producing ability and can metabolize fatty acid(s) when used as the carbon source.

Examples of the bacterium of Enterobacteriaceae family can include bacteria belonging to the genera *Escherichia, Enterobacter, Erwinia, Klebsiella, Pantoea, Photorhabdus, Providencia, Salmonella, Serratia, Shigella, Morganella*, and *Yersinia*. In specific examples, bacteria classified into the Enterobacteriaceae family based on the classification method used by the database of the NCBI (National Center for Biotechnology Information) (www.ncbi.nlm.nih.gov/Taxonomy/Browser/wwwtax.cgi?id=91347) can be used.

The bacteria belonging to the genus *Escherichia* are not particularly limited, but can include bacteria classified into the genus *Escherichia* based on the classification known to microbiologists. Examples of a bacterium belonging to the genus *Escherichia* to be used in the present invention can include, but are not limited to, *Escherichia coli* (*E. coli*).

The bacteria belonging to the genus *Escherichia* that can be used in accordance with the presently disclosed subject matter are not particularly limited, but can include the bacterial strains described in Table 1 of Bachmann et al. (Bachmann, B. J. 1996. p. 2460-2488. In F. D. Neidhardt (ed.), *Escherichia coli* and *Salmonella* Cellular and Molecular Biology/Second Edition, American Society for Microbiology Press, Washington, D.C). Specific examples can include *Escherichia coli* W3110 (ATCC 27325) and *Escherichia coli* MG1655 (ATCC 47076) derived from a prototype wild-type K-12 strain.

These strains can be obtained from the American Type Culture Collection (ATCC) (Address: P.O. Box 1549, Manassas, Va. 20108, 1, United States of America). That is, an accession number is given to each strain, and a desirable bacterial strain can be ordered by referencing the accession number. The accession number of each strain may be found in the catalogue of the American Type Culture Collection.

The bacteria belonging to the genus *Pantoea* can include bacteria classified into the genus *Pantoea* based on the classification known to microbiologists. In recent years, some of *Enterobacter agglomerans* bacteria were reclassified into *Enterobacter agglomerans, Pantoea ananatis, Pantoea stewartii*, etc. based on the nucleotide sequence analysis of 16S rRNA (Int. J. Syst. Bacteriol. 1993. 43: 162-173). Bacteria belonging to the genus *Pantoea* can include such bacteria reclassified into the genus *Pantoea*.

In accordance with the presently disclosed subject matter, the bacteria having an L-amino acid-producing ability can include bacteria having an ability to produce and secrete an L-amino acid in the medium when it is cultured in the medium. In addition, the bacteria can have an ability to produce and secrete an L-amino acid in an amount of 0.5 g/L or more or in an amount of 1.0 g/L or more into the medium. The L-amino acid can include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine. Among these, L-threonine, L-lysine, L-phenylalanine, L-tryptophan, L-valine, L-leucine, L-isoleucine, and L-methionine can be preferable. In particular, L-threonine and L-lysine can be preferable.

In a method in accordance with the presently disclosed subject matter, L-amino acid-producing bacteria that have been reported so far can be used as long as they can assimilate fatty acid.

Hereinafter, L-amino acid-producing bacteria that can be used in accordance with the presently disclosed subject matter will be described.

L-Threonine-Producing Bacteria

Examples of L-threonine-producing bacteria and parent strains which can be used to derive the L-threonine-producing bacteria can include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The TDH-6 strain is deficient in the thrC gene, as well as being sucrose-assimilative, and the ilvA gene has a leaky mutation. This strain also has a mutation in the rhtA gene, which imparts resistance to high concentrations of threonine or homoserine. The B-3996 strain contains pVIC40, which was obtained by inserting the thrA*BC operon, which includes a mutant thrA gene, into a RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russian Federation) under the accession number RIA 1867. This strain was also deposited in the Russian National Collection of Industrial Microorganisms (VKPM) (Russia, 117545 Moscow 1, Dorozhny proezd. 1) on Apr. 7, 1987 under the accession number B-3996.

*E. coli* VKPM B-5318 (EP 0593792B) can also be used as an L-threonine-producing bacterium. The B-5318 strain is prototrophic with regard to isoleucine, and a temperature-sensitive lambda-phage C1 repressor and PR promoter replaces the regulatory region of the threonine operon in plasmid pVIC40. The VKPM B-5318 strain was deposited in the Russian National Collection of Industrial Microorganisms (VKPM: Russia, 117545 Moscow 1, Dorozhny proezd. 1) on May 3, 1990 under accession number of VKPM B-5318.

L-threonine-producing bacteria can be additionally modified to enhance expression of one or more of the following genes:
  the mutant thrA gene which codes for aspartokinase homoserine dehydrogenase I resistant to feed back inhibition by threonine;
  the thrB gene which codes for homoserine kinase;

the thrC gene which codes for threonine synthase;
the rhtA gene which codes for a putative transmembrane protein;
the asd gene which codes for aspartate-α-semialdehyde dehydrogenase; and
the aspC gene which codes for aspartate aminotransferase (aspartate transaminase).

The sequence of the thrA gene of *Escherichia coli* which encodes aspartokinase homoserine dehydrogenase I has been elucidated (nucleotide positions 337 to 2799, GenBank accession NC_000913.2, gi: 49175990). The thrA gene is located between the thrL and thrB genes on the chromosome of *E. coli* K-12. The nucleotide sequence of the thrB gene of *Escherichia coli* which encodes homoserine kinase has been elucidated (nucleotide positions 2801 to 3733, GenBank accession NC_000913.2, gi: 49175990). The thrB gene is located between the thrA and thrC genes on the chromosome of *E. coli* K-12. The nucleotide sequence of the thrC gene of *Escherichia coli* which encodes threonine synthase has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes function together as a single threonine operon. To enhance the expression of the threonine operon, the attenuator region which affects the transcription can be removed from the operon (WO2005/049808, WO2003/097839).

The mutated thrA gene which encodes feedback-resistant aspartokinase homoserine dehydrogenase I, as well as the thrB and thrC genes can be obtained as one operon from the well-known plasmid pVIC40. This plasmid is present in the threonine producing *E. coli* strain VKPM B-3996, and is described in detail in U.S. Pat. No. 5,705,371.

The rhtA gene is at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The sequence expressing a protein encoded by the ORF1 has been designated the rhtA gene (rht: resistance to homoserine and threonine). Also, the rhtA23 mutation is an A-for-G substitution at position-1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The nucleotide sequence of the asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) by utilizing primers based on the nucleotide sequence of the gene. The asd genes from other microorganisms can be obtained in a similar manner.

Also, the nucleotide sequence of the aspC gene of *E. coli* has already been elucidated (nucleotide positions 983742 to 984932, GenBank accession NC_000913.1, gi:16128895), and can be obtained by PCR. The aspC genes from other microorganisms can be obtained in a similar manner.

L-Lysine-Producing Bacteria

Examples of L-lysine-producing bacteria belonging to the genus *Escherichia* can include mutants having resistance to an L-lysine analogue. The L-lysine analogue inhibits growth of bacteria belonging to the genus *Escherichia*, but this inhibition is fully or partially desensitized when L-lysine is present in a medium. Examples of the L-lysine analogue can include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine can include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 can be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of L-lysine-producing bacteria and parent strains for deriving L-lysine-producing bacteria also can include strains in which expression of one or more genes encoding an L-lysine biosynthetic enzyme are enhanced. Examples of the enzymes involved in L-lysine biosynthesis can include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semi-aldehyde dehydrogenease (asd), and aspartase (aspA) (EP 1253195 A). In addition, the L-lysine-producing strains can have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

It is known that wild-type DDPS derived from *Escherichia coli* is regulated by feedback inhibition by L-lysine, while wild-type aspartokinase derived from *Escherichia coli* is regulated by suppression and feedback inhibition by L-lysine. Therefore, when using dapA and lysC, mutated forms of these genes are preferably used so that the enzymes encoded by the genes are not subject to feedback inhibition.

An example of a DNA encoding a mutant DDPS desensitized to feedback inhibition by L-lysine can include a DNA encoding a DDPS which has an amino acid sequence in which the histidine at position 118 is replaced by tyrosine. Meanwhile, an example of a DNA encoding mutant aspartokinase III (AKIII) desensitized to feedback inhibition by L-lysine can include a DNA encoding an AKIII having an amino acid sequence in which the threonine at position 352, the glycine at position 323, and the methionine at position 318 are replaced by isoleucine, asparagine and isoleucine, respectively (U.S. Pat. No. 5,661,012 and U.S. Pat. No. 6,040,160). Such mutant DNAs can be obtained by a site-specific mutation using PCR or the like.

Wide host-range plasmids RSFD80, pCAB1, and pCABD2 are known to contain a mutant dapA gene encoding a mutant DDPS and a mutant lysC gene encoding a mutant AKIII (U.S. Pat. No. 6,040,160). *Escherichia coli* JM109 strain transformed with RSFD80 was named AJ12396 (U.S. Pat. No. 6,040,160), and the strain was deposited at the National Institute of Bioscience and Human-Technology, Agency of Industrial Science and Technology, Ministry of International Trade and Industry (currently, International Patent Organism Depositary, National Institute of Advanced Industrial Science and Technology) on Oct. 28, 1993 and given an accession number of FERM P-13936, and the deposit was then converted to an international deposit under the provisions of Budapest Treaty on Nov. 1, 1994 and given an accession number of FERM BP-4859. RSFD80 can be obtained from AJ12396 strain by a conventional method.

Examples of L-lysine-producing bacteria and parent strains for deriving L-lysine-producing bacteria also can include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine can include homoserine dehydrogenase (WO 95/23864), lysine decarboxylase (U.S. Pat. No. 5,827,698), and the malic enzyme (WO2005/010175).

In *Escherichia coli*, lysine decarboxylases are encoded by the cadA gene (GenBank Accession No. NP_418555, SEQ ID NO: 5) and ldcC gene (GenBank Accession No. NP_414728, SEQ ID NO: 7) (WO 96/17930), so these genes may be disrupted to enhance L-lysine-producing ability. DNA molecules homologous to the cadA gene and ldcC gene can be used as long as they can induce homologous recombination with the cadA gene and ldcC gene on the chromosome of a host bacterium. For example, a DNA molecule homologous to the cadA gene may hybridize to a complementary strand of SEQ ID NO: 5 under stringent conditions, and a DNA molecule homologous to the ldcC gene may hybridize to a complementary strand of SEQ ID NO: 7 under stringent conditions.

Herein, the term "stringent conditions" refers to conditions where a so-called specific hybrid is formed and non-specific hybrid is not formed. Exemplary stringent conditions can include conditions where DNAs having high homology, for example, DNAs having homology of at least 80%, at least 90%, at least 95%, or at least 97% hybridize with each other, and DNAs having homology of less than 80% do not hybridize with each other. Specific examples thereof can include washing in general Southern hybridization, i.e., washing at the salt concentration of 1×SSC, 0.1% SDS, or a salt concentration of 0.1×SSC, 0.1% SDS, at 60° C., or at 68° C. This washing can performed once, twice or three times.

L-Cysteine-Producing Bacteria

Examples of L-cysteine-producing bacteria and parent strains which can be used to derive L-cysteine-producing bacteria can include, but are not limited to, strains belonging to the genus *Escherichia*, such as *E. coli* JM15 which has been transformed with different cysE alleles coding for feedback-resistant serine acetyltransferases (U.S. Pat. No. 6,218,168, Russian patent application 2003121601), *E. coli* W3110 which over-expresses genes which encode proteins suitable for secreting toxic substances (U.S. Pat. No. 5,972,663), *E. coli* strains with decreased cysteine desulfohydrase activity (JP11155571A2); *E. coli* W3110 with increased activity of a positive transcriptional regulator for the cysteine regulon encoded by the cysB gene (WO0127307A1), and the like.

L-Leucine-Producing Bacteria

Examples of L-leucine-producing bacteria and parent strains which can be used to derive L-leucine-producing bacteria can include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the genetic engineering method described in WO96/06926; *E. coli* H-9068 (JP 8-70879 A), and the like.

The L-leucine-producing ability can be improved by enhancing the expression of one or more genes involved in L-leucine biosynthesis. Examples of these genes can include those of the leuABCD operon. The leuABCD operon can include a leuA gene which has been mutated so that it encodes isopropylmalate synthase which is resistant to feedback inhibition by L-leucine (U.S. Pat. No. 6,403,342). In addition, bacteria in accordance with the presently disclosed subject matter can be improved by enhancing the expression of one or more genes coding for proteins which excrete L-amino acids from the bacterial cell. Examples of such genes can include the b2682 and b2683 genes (ygaZH genes) (EP 1239041 A2).

L-Histidine-Producing Bacteria

Examples of L-histidine-producing bacteria and parent strains which can be used to derive L-histidine-producing bacteria can include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of L-histidine-producing bacteria and parent strains which can be used to derive L-histidine-producing bacteria also can include strains in which expression of one or more genes encoding an L-histidine biosynthetic enzyme are enhanced. Examples of these L-histidine-biosynthetic enzymes can include ATP phosphoribosyltransferase (hisG), phosphoribosyl AMP cyclohydrolase (hisI), phosphoribosyl-ATP pyrophosphohydrolase (hisIE), phosphoribosyl-formimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the genes encoding the L-histidine biosynthetic enzyme (hisG, hisBHAFI) are inhibited by L-histidine. Therefore the L-histidine-producing ability can also be efficiently enhanced by introducing a mutation which induces resistance to feedback inhibition into ATP phosphoribosyltransferase (hisG) (Russian Patent Nos. 2003677 and 2119536). Specific examples of strains having an L-histidine-producing ability can include *E. coli* FERM-P 5038 and 5048 which have been transformed with a vector carrying a DNA encoding an L-histidine-biosynthetic enzyme (JP 56-005099 A), *E. coli* strains transformed with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of L-glutamic acid-producing bacteria and parent strains which can be used to derive L-glutamic acid-producing bacteria can include, but are not limited to, strains belonging to the genus *Escherichia*, such as *E. coli* VL334thrC⁺ (EP 1172433). *E. coli* VL334 (VKPM B-1641) is auxotrophic for L-isoleucine and L-threonine and is mutated in the thrC and ilvA genes (U.S. Pat. No. 4,278,765). A wild-type allele of the thrC gene was transferred by general transduction using a bacteriophage P1 grown on the wild-type E. coli strain K12 (VKPM B-7). As a result, an L-isoleucine auxotrophic strain VL334thrC+ (VKPM B-8961) was obtained.

Examples of L-glutamic acid-producing bacteria and parent strains for deriving the L-glutamic acid-producing bacteria can include, but are not limited to, strains in which expression of one or more genes encoding an L-glutamic acid biosynthetic enzyme are enhanced. Examples of the enzymes involved in L-glutamic acid biosynthesis can include glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA), phosphoglycerate kinase (pgk), glyceraldehyde-3-phosphate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced can include those disclosed in EP1078989A, EP955368A, and EP952221A.

Examples of L-glutamic acid-producing bacteria and parent strains which can be used to derive the L-glutamic acid-producing bacteria also can include strains which have a decreased or eliminated activity of an enzyme that catalyzes synthesis of a compound other than L-glutamic acid, and branches off from the L-glutamic acid biosynthesis pathway. Examples of such enzymes can include isocitrate lyase, α-ketoglutarate dehydrogenase, phosphotransacetylase, acetate kinase, acetohydroxy acid synthase, acetolactate synthase, formate acetyltransferase, lactate dehydrogenase, and glutamate decarboxylase. Bacteria belonging to the genus Escherichia deficient in α-ketoglutarate dehydrogenase activity or having a reduced α-ketoglutarate dehydrogenase activity and methods for obtaining them are described in U.S. Pat. Nos. 5,378,616 and 5,573,945.

By way of example, these strains can include the following:
E. coli W3110sucA::Kmr
E. coli AJ12624 (FERM BP-3853)
E. coli AJ12628 (FERM BP-3854)
E. coli AJ12949 (FERM BP-4881)

E. coli W3I1OsucA::Kmr is obtained by disrupting the α-ketoglutarate dehydrogenase gene (hereinafter referred to as the "sucA gene") of E. coli W3110. This strain is completely deficient in α-ketoglutarate dehydrogenase.

Other examples of L-glutamic acid-producing bacterium can include those which belong to the genus Escherichia and have resistance to an aspartic acid antimetabolite. These strains can also be deficient in α-ketoglutarate dehydrogenase activity and include, for example, E. coli AJ13199 (FERM BP-5807) (U.S. Pat. No. 5,908,768), FERM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria can include mutant strains belonging to the genus Pantoea which are deficient in α-ketoglutarate dehydrogenase activity or have decreased α-ketoglutarate dehydrogenase activity, and can be obtained as described above. Such strains can include Pantoea ananatis AJ13356 (U.S. Pat. No. 6,331,419). Pantoea ananatis AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. Pantoea ananatis AJ13356 is deficient in α-ketoglutarate dehydrogenase activity as a result of the disruption of the αKGDH-E1 subunit gene (sucA). The above strain was identified as Enterobacter agglomerans when it was isolated and deposited as the Enterobacter agglomerans AJ13356. However, it was recently re-classified as Pantoea ananatis on the basis of nucleotide sequencing of 16S rRNA and so forth. Although AJ13356 was deposited at the aforementioned depositary as Enterobacter agglomerans, for the purposes of this disclosure, they are described as Pantoea ananatis.

L-Phenylalanine-Producing Bacteria

Examples of L-phenylalanine-producing bacteria and parent strains which can be used to derive L-phenylalanine-producing bacteria can include, but are not limited to, strains belonging to the genus Escherichia, such as E. coli AJ12739 (tyrA::Tn10, tyrR) (VKPM B-8197); E. coli HW1089 (ATCC 55371) harboring the pheA34 gene (U.S. Pat. No. 5,354,672); E. coli MWEC101-b (KR8903681); E. coli NRRL B-12141, NRRL B-12145, NRRL B-12146 and NRRL B-12147 (U.S. Pat. No. 4,407,952). Also, as an L-phenylalanine-producing strain, E. coli K-12 [W3110 (tyrA)/pPHAB (FERM BP-3566), E. coli K-12 [W3110 (tyrA)/pPHAD] (FERM BP-12659), E. coli K-12 [W3110 (tyrA)/pPHATerm] (FERM BP-12662) and E. coli K-12 [W3110 (tyrA)/pBR-aroG4, pACMAB] named as AJ 12604 (FERM BP-3579) can be used (EP 488-424 B1). Furthermore, L-phenylalanine producing bacteria belonging to the genus Escherichia which have an enhanced activity of the protein encoded by the yedA gene or the yddG gene also can be used (U.S. patent applications 2003/0148473 A1 and 2003/0157667 A1).

L-Tryptophan-Producing Bacteria

Examples of L-tryptophan-producing bacteria and parent strains which can be used to derive the L-tryptophan-producing bacteria can include, but are not limited to, strains belonging to the genus Escherichia, such as E. coli JP4735/pMU3028 (DSM10122) and JP6015/pMU91 (DSM10123) deficient in the tryptophanyl-tRNA synthetase encoded by mutant trpS gene (U.S. Pat. No. 5,756,345); E. coli SV164 (pGH5) having a serA allele encoding phosphoglycerate dehydrogenase resistant to feedback inhibition by serine and a trpE allele encoding anthranilate synthase resistant to feedback inhibition by tryptophan (U.S. Pat. No. 6,180,373); E. coli AGX17 (pGX44) (NRRL B-12263) and AGX6(pGX50) aroP (NRRL B-12264) deficient in the enzyme tryptophanase (U.S. Pat. No. 4,371,614); E. coli AGX17/pGX50, pACKG4-pps in which a phosphoenolpyruvate-producing ability is enhanced (WO9708333, U.S. Pat. No. 6,319,696), and the like. Furthermore, L-tryptophan producing bacteria belonging to the genus Escherichia which have an enhanced activity of the protein encoded by the yedA gene or the yddG gene also can be used (U.S. patent applications 2003/0148473 A1 and 2003/0157667 A1).

Examples of L-tryptophan-producing bacteria and parent strains which can be used to derive the L-tryptophan-producing bacteria also can include strains in which one or more activities of the enzymes selected from anthranilate synthase (trpE), phosphoglycerate dehydrogenase (serA), and tryptophan synthase (trpAB) are enhanced. The anthranilate synthase and phosphoglycerate dehydrogenase are both subject to feedback inhibition by L-tryptophan and L-serine, so a mutation which results in desensitizing the feedback inhibition may be introduced into these enzymes. Specific examples of strains having such a mutation can include an *E. coli* SV164 which harbors desensitized anthranilate synthase and a strain obtained by transforming the plasmid pGH5 into *E. coli* SV164 (WO 94/08031), which contains a serA gene which has been mutated so that it encodes feedback-desensitized phosphoglycerate dehydrogenase.

Examples of L-tryptophan-producing bacteria and parent strains for deriving the L-tryptophan-producing bacteria also can include strains transformed with the tryptophan operon which contains a gene encoding desensitized anthranilate synthase (JP 57-71397 A, JP 62-244382 A, U.S. Pat. No. 4,371,614). Moreover, L-tryptophan-producing ability can be imparted by enhancing expression of a gene which encodes tryptophan synthase, among tryptophan operons (trpBA). The tryptophan synthase consists of α and β subunits which are encoded by trpA and trpB, respectively. In addition, L-tryptophan-producing ability can be improved by enhancing expression of the isocitrate lyase-malate synthase operon (WO2005/103275).

L-Proline-Producing Bacteria

Examples of L-proline-producing bacteria and parent strains which can be used to derive L-proline-producing bacteria can include, but are not limited to, strains belonging to the genus *Escherichia*, such as *E. coli* 702ilvA (VKPM B-8012) which is deficient in the ilvA gene and is able to produce L-proline (EP 1172433).

The L-proline-producing ability can be improved by enhancing the expression of one or more genes involved in L-proline biosynthesis. Examples of genes for L-proline producing bacteria can include the proB gene coding for glutamate kinase which is desensitized to feedback inhibition by L-proline (DE Patent 3127361). In addition, bacteria in accordance with the presently disclosed subject matter can be improved by enhancing the expression of one or more genes coding for proteins excreting L-amino acid from the bacterial cell. Such genes include the b2682 and b2683 genes (ygaZH genes) (EP1239041 A2).

Examples of bacteria belonging to the genus *Escherichia* which have an activity to produce L-proline can include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15th Miami winter symposium, 1983, p. 34), and the like.

L-Arginine-Producing Bacteria

Examples of L-arginine-producing bacteria and parent strains which can be used to derive L-arginine-producing bacteria can include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which the argA gene encoding N-acetylglutamate synthetase is introduced (EP1170361A1), and the like.

Examples of L-arginine-producing bacteria and parent strains which can be used to derive L-arginine producing bacteria also can include strains in which expression of one or more genes encoding an L-arginine biosynthetic enzyme are enhanced. Examples of the L-arginine biosynthetic enzymes include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Example of L-valine-producing bacteria and parent strains which can be used to derive L-valine-producing bacteria can include, but are not limited to, strains which have been modified to overexpress the ilvGMEDA operon (U.S. Pat. No. 5,998,178). It is possible to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased. Examples of L-valine-producing bacteria also can include mutants of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 113545 Moscow, 1 Dorozhny Proezd.) on Jun. 24, 1988 under accession number VKPM B-4411.

Furthermore, mutants requiring lipoic acid for growth and/or lacking $H^+$-ATPase can also be used (WO96/06926).

L-Isoleucine-Producing Bacteria

Examples of L-isoleucine-producing bacteria and parent strains which can be used to derive L-isoleucine producing bacteria can include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used (JP 2-458 A, FR 0356739, and U.S. Pat. No. 5,998,178).

L-Methionine-Producing Bacteria

Examples of L-methionine-producing bacteria and parent strains which can be used to derive L-methionine producing bacteria can include, but are not limited to, L-threonine-auxotrophic mutant strain and norleucine-resistant mutant strain (JP 2000-139471 A), a methionine repressor-deficient strain and recombinant strains transformed with genes encoding L-methionine biosynthetic enzymes such as homoserine transsuccinylase and cystathionine γ-synthase (JP 2000-139471 A).

EXAMPLES

Hereinafter, reference is made to the following non-limiting Examples in accordance with the presently disclosed subject matter. In the Examples, oleic acid sodium salt ($C_{17}H_{33}$COONa), palmitic acid sodium salt ($C_{15}H_{31}$COONa) (both manufactured by Nacalai Tesque, Inc.), myristic acid sodium salt ($C_{13}H_{27}$COONa) (SIGMA) and linoleic acid ($C_{17}H_{31}$COOH) (Nacalai Tesque, Inc.) were used.

Example 1

Culture for Producing L-Threonine

*Escherichia coli* B-5318, an L-threonine-producing strain, was cultured on LB agar medium (10 g/L tryptone, 5 g/L yeast extract, 10 g/L NaCl, and 15 g/L agar) containing 20 mg/L of streptomycin sulfate at 37° C. for 24 hours. The cells grown on the agar medium were scraped off and inoculated into a 500-ml baffle flask containing 20 mL of a fermentation medium, followed by culturing at a temperature of 40° C. for 24 hours.

The composition of the fermentation medium used for the L-threonine fermentation is shown below. Sodium oleate was added to the fermentation medium as the carbon source. The total carbon content was adjusted to 20 g/L in each medium.

Escherichia bacterium L-threonine fermentation medium:

| | |
|---|---|
| Carbon source | 20 g/L |
| Yeast extract | 2 g/L |
| $FeSO_4 \cdot 7H_2O$ | 10 mg/L |
| $MnSO_4 \cdot 4H_2O$ | 10 mg/L |
| $KH_2PO_4$ | 1.0 g/L |
| $MgSO_4 \cdot 7H_2O$ | 1 g/L |
| $(NH_4)_2SO_4$ | 16 g/L |
| Streptomycin sulfate | 20 mg/L |

The medium was adjusted to pH 7.0 with KOH and sterilized in an autoclave at 120° C. for 20 minutes. The carbon source and $MgSO_4 \cdot 7H_2O$ were separately sterilized and mixed. $CaCO_3$ was added after dry heat sterilization.

After 24 hours, the culture supernatants were analyzed by liquid chromatography to determine the amount of L-threonine. Growth could not be determined based on the turbidities (ODs), and therefore, culture media diluted to appropriate concentrations were applied onto LB plates, followed by determination of the number of viable cells. The results are shown in Table 1 as the mean of duplicate cultures.

When the culture was performed using only oleic acid as the carbon source, a substantial amount of L-threonine accumulated.

TABLE 1

Results of culture of the L-threonine-producing bacterium

| Carbon source | Culture time (h) | Viable cells ($10^8$/ml) | L-threonine (g/l) |
|---|---|---|---|
| Oleic acid | 24 | 7.3 | 3.8 |

Example 2

<2-1> Construction of a Strain with Disrupted Lysine Decarboxylase-Encoding Genes (cadA and ldcC)

A strain which produces no lysine decarboxylase was constructed. The lysine decarboxylases are encoded by the cadA gene (GenBank Accession No. NP-418555, SEQ ID NO: 5) and the ldcC gene (GenBank Accession No. NP-414728, SEQ ID NO: 7) (WO 96/17930). Escherichia coli WC196 (FERM BP-5252), which is an AEC-resistant L-lysine-producing strain, was used as a parent strain (WO96/17930).

The cadA and ldcC gene were disrupted by the method developed by Datsenko and Wanner, which is called "Red-driven integration" (Proc. Natl. Acad. Sci. USA, 2000, vol. 97, No. 12, p6640-6645), and by an excision system derived from λ phage (J. Bacteriol. 2002 September; 184(18): 5200-3. Interactions between integrase and excisionase in the phage lambda excisive nucleoprotein complex. Cho E H, Gumport R I, Gardner J F.). "Red-driven integration" makes it possible to construct a gene-disrupted strain in one step by employing a PCR product obtained by using as primers synthetic oligonucleotides designed to have a part of the targeted gene on their 5'-ends, and a part of an antibiotic-resistance gene on their 3'-ends. Combining this method with the λ phage-derived excision system permits the removal of the antibiotic-resistance gene that becomes incorporated into the gene-disrupted strain (JP2005-058227).

<2-2> Disruption of the cadA Gene

The pMW118-attL-Cm-attR plasmid (WO2005/010175) was used as a template for PCR. pMW118-attL-Cm-attR was obtained by inserting the attL and attR genes, which are attachment sites for λ phage, and the cat gene, which is an antibiotic resistance gene, into pMW118 (Takara Bio Inc.) The genes are arranged in the following order: attL-cat-attR.

PCR was performed using, as primers, the synthetic oligonucleotides shown in SEQ ID NOS: 1 and 2, which have sequences corresponding to attL and attR on their 3'-ends and a sequence corresponding to a part of the targeted cadA gene on their 5'-ends.

The amplified PCR product was purified on an agarose gel and introduced into the Escherichia coli WC1-96 strain by electroporation. This strain harbors pKD46 which has temperature-sensitive replicability. pKD46 (Proc. Natl. Acad. Sci. USA, 2000, vol. 97, No. 12, p6640-6645) contains a DNA fragment of 2,154 nucleotides derived from λ phage which contains the Red recombinase-encoding genes (γ, β, and exo genes) of the λ Red homologous recombination system, which is controlled by an arabinose-inducible ParaB promoter (GenBank/EMBL Accession No. J02459, nucleotide numbers 31088 to 33241). pKD46 is used to integrate the PCR product into the chromosome of the WC1-96 strain.

Competent cells for electroporation were prepared as follows. That is, cells of the Escherichia coli WC1-96 strain with pKD46 were cultured overnight at 30° C. in LB medium containing 100 mg/L ampicillin, and then diluted 100-fold with 5 mL of SOB medium (Molecular Cloning: Laboratory manual, 2nd edition, Sambrook, J. et al., Cold Spring Harbor Laboratory Press (1989)) containing ampicillin (20 mg/L) and L-arabinose (1 mM). The diluted cells were grown with aeration at 30° C. until the OD600 reached about 0.6, and then concentrated 100-fold and washed three times with 10% glycerol so that the cells were available for electroporation. The electroporation was performed with 70 µL of the competent cells and about 100 ng of the PCR product. After the electroporation, 1 mL of SOC medium (Molecular Cloning: Laboratory manual, 2nd edition, Sambrook, J. et al., Cold Spring Harbor Laboratory Press (1989)) was added to the cells, and cells were cultured at 37° C. for 2.5 hours, and then subjected to plate culture onto L-agar medium containing Cm (chloramphenicol) (25 mg/L), to thereby select Cm-resistant recombinant strains. Subsequently, to remove the plasmid pKD46, the cells were subcultured twice at 42° C. on L-agar medium containing Cm, and ampicillin resistance of the resultant colonies were examined, to thereby yield ampicillin-sensitive strains in which the pKD46 was cured.

Deletion of the cadA gene in the mutant strain, which had been identified by the chloramphenicol-resistance gene, was confirmed by PCR. The cadA-disrupted strain was named WC196ΔcadA::att-cat.

Subsequently, the helper plasmid pMW-intxis-ts (WO2005/010175) was used to remove the att-cat gene which had been introduced into the cadA gene. The plasmid pMW-intxis-ts carries a gene encoding the integrase (Int) of λ phage, and the gene encoding excisionase (Xis), and has temperature-sensitive replicability.

Competent cells of the WC196ΔcadA::att-cat strain were prepared by a conventional method, and were then transformed with the helper plasmid pMW-intxis-ts, and then subjected to plate culture at 30° C. on L-agar medium containing 50 mg/L ampicillin, to thereby select ampicillin-resistant strains.

Subsequently, to remove the plasmid pMW-intxis-ts, the cells were subcultured twice at 42° C. on L-agar medium, and ampicillin resistance and chloramphenicol resistance of the resulting colonies were examined, to thereby yield a chloramphenicol- and ampicillin-sensitive strain, in which the cadA gene was disrupted, and att-cat and the pMW-intxis-ts were removed. The strain was named WC196ΔcadA.

<2-3> Disruption of the ldcC Gene in the WC196ΔcadA strain

The ldcC gene in the WC196ΔcadA strain was disrupted by using oligonucleotides of SEQ ID NOS: 3 and 4 as primers in the same way as described above. In this way, a cadA and ldcC-disrupted strain named WC196ΔcadAΔldcC was obtained.

<2-4> Introduction of a Plasmid Containing Lysine Biosynthetic Genes into the WC196ΔcadAΔldcC strain WC196ΔcadAΔldcC strain was transformed with a plasmid for lysine production named pCABD2 (WO 95/16042), which carries the dapA gene, dapB gene, lysC gene and ddh gene, to thereby yield the WC196ΔcadAΔldcC/pCABD2 strain (hereinafter, referred to as WC196LC/pCABD2).

The WC196LC/pCABD2 strain was cultured at 37° C. in L-medium containing 50 mg/L of ampicillin and 20 mg/L of streptomycin until the final $OD_{600}$ reached about 0.6, and then an equal volume of 40% glycerol solution was added to the culture, followed by stirring. Then, the resulting suspension was dispensed in appropriate amounts and stored at −80° C., which was used as a glycerol stock.

Example 3

Culture of the L-Lysine-Producing Strain of *Escherichia* Bacterium

The glycerol stock of the WC196LC/pCABD2 strain was thawed, and 100 μL of the stock was uniformly applied to an L-plate containing 25 mg/L streptomycin, and the cells were cultured at 37° C. for 24 hours. About one-eighth of the cells on the plate were inoculated into 20 mL of a fermentation medium containing 25 mg/L streptomycin in a 500-mL Sakaguchi flask, followed by culturing at 37° C. for 48 hours using a reciprocal shaker.

The composition of the fermentation medium used for the L-lysine fermentation is shown below. Sodium oleate or a mixture of sodium oleate and sodium palmitate was dissolved into the fermentation medium as the carbon source with or without a nonionic surfactant, poly(oxyethylene) sorbitan monooleate (Tween 80) (manufactured by Nacalai Tesque, Inc.). The total content of the carbon source in each medium was adjusted to 20 g/L.

*Escherichia* Bacterium L-Lysine Fermentation Medium:

| | |
|---|---|
| Carbon source | 20 g/L |
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.01 g/L |
| Yeast extract | 2.0 g/L |
| $CaCO_3$ (Japanese Pharmacopoeia) | 30 g/L |

The medium was adjusted to pH 7.0 with KOH and sterilized in an autoclave at 120° C. for 20 minutes. The carbon source and $MgSO_4 \cdot 7H_2O$ were separately sterilized and mixed. $CaCO_3$ was added after dry heat sterilization.

After 24 and 48 hours, the amount of L-lysine in the culture supernatants was determined using a bioanalyzer AS210 (Sakura Finetechnical Co., Ltd.). Growth could not be determined based on the turbidities (ODs), and therefore, culture media diluted to appropriate concentrations were applied onto LB plates, followed by determination of the number of viable cells. The results are shown in Table 2 as the mean duplicate cultures.

When the culture was performed under the above-mentioned conditions using oleic acid as the carbon source, L-lysine was produced, and addition of Tween 80 significantly increased the amount of accumulated L-lysine. When using a mixture of equal amounts of palmitic acid and oleic acid as the carbon sources, the amount of accumulated L-lysine significantly increased compared with when using only oleic acid as the carbon source, and the L-lysine production further increased by addition of Tween 80.

TABLE 2

Results of culture of the L-lysine-producing strain

| Carbon source | Additive | Culture time (h) | Viable cells ($10^8$/ml) | L-lysine (g/l) |
|---|---|---|---|---|
| Oleic acid 20 g/l | None | 24 | 1.4 | 1.5 |
| | | 48 | 0.4 | 1.8 |
| Oleic acid 20 g/l | 0.5% Tween80 | 24 | 0.6 | 2.3 |
| | | 48 | 1.4 | 2.8 |
| Palmitic acid 10 g/l + Oleic acid 10 g/l | None | 24 | 0.6 | 2.3 |
| | | 48 | 1.3 | 2.7 |
| Palmitic acid 10 g/l + Oleic acid 10 g/l | 0.5% Tween80 | 24 | 0.8 | 2.5 |
| | | 48 | 1.3 | 3.2 |

Example 4

Culture of the L-Lysine-Producing Strain of *Escherichia* Bacterium Using Fatty Acid as Carbon Source Treated with Sonication The glycerol stock of WC196LC/pCABD2 strain was thawed, and 100 μL of the stock was uniformly applied to an L-plate containing 25 mg/L streptomycin, and the cells were cultured at 37° C. for 24 hours. About one-eighth of the cells on the plate were inoculated into 20 mL of the fermentation medium described below containing 25 mg/L streptomycin in a 500-mL Sakaguchi flask, followed by culturing at 37° C. for 48 hours using a reciprocal shaker.

The composition of the fermentation medium used for the L-lysine fermentation is shown below. Sodium oleate, or a mixture of sodium oleate and sodium palmitate was dissolved into the fermentation medium as the carbon source with or without the surfactant Tween 80, and followed by sonication treatment (for 5 minutes using UT-250 manufactured by SHARP CORPORATION). The total content of the carbon source in each medium was adjusted to 20 g/L.

*Escherichia* Bacterium L-Lysine Fermentation Medium:

| Carbon source | 20 g/L |
|---|---|
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.01 g/L |
| Yeast extract | 2.0 g/L |
| $CaCO_3$ (Japanese Pharmacopoeia) | 30 g/L |

The medium was adjusted to pH 7.0 with KOH and sterilized in an autoclave at 120° C. for 20 minutes. The carbon source and $MgSO_4 \cdot 7H_2O$ were separately sterilized and mixed. $CaCO_3$ was added after dry heat sterilization.

After 24 hours and 48 hours, the amount of L-lysine in the culture supernatants was determined using a bioanalyzer AS210 (Sakura Finetechnical Co., Ltd.). Growth could not be determined based on the turbidities (ODs), and therefore, culture media diluted to appropriate concentrations were applied onto LB plates, followed by determination of the number of viable cells. The results are shown in Table 3 as the mean of duplicate cultures.

The conditions for the culture of Example 4 (Table 3) includes a sonication step in addition to the culture conditions of Example 3 (Table 2), and the effects of the sonication can be understood by comparing the results of Table 3 with Table 2. When using oleic acid as the carbon source, the amount of L-lysine produced significantly increased by sonication whether with or without the addition of Tween 80. Moreover, when using a mixture of equal amounts of palmitic acid and oleic acid as the carbon source, sonication decreased the amount of L-lysine which accumulated in the absence of Tween 80, while sonication increased the amount of L-lysine which accumulated in the presence of Tween 80.

TABLE 3

Results of culture of the L-lysine-producing strain using sonicated fatty acid

| Carbon source | Additive | Culture time (h) | Viable cells ($10^8$/ml) | L-lysine (g/l) |
|---|---|---|---|---|
| Oleic acid 20 g/l | None | 24 | 5.5 | 2.2 |
| | | 48 | 5.0 | 2.4 |
| Oleic acid 20 g/l | 0.5% Tween80 | 24 | 0.4 | 2.8 |
| | | 48 | 0.6 | 3.6 |
| Palmitic acid 10 g/l + Oleic acid 10 g/l | None | 24 | 0.04 | 0.12 |
| | | 48 | <0.01 | 0.15 |
| Palmitic acid 10 g/l + Oleic acid 10 g/l | 0.5% Tween80 | 24 | 1.7 | 3.1 |
| | | 48 | 9.8 | 3.9 |

Example 5

Culture of the L-Lysine-Producing Strain of *Escherichia* Bacterium Using a Fatty Acid and a Surfactant The glycerol stock of WC196LC/pCABD2 strain was thawed, and 100 µL of the stock was uniformly applied onto an L-plate containing 25 mg/L streptomycin, and the cells were cultured at 37° C. for 24 hours. About one-eighth of the cells on the plate were inoculated into 20 mL of the fermentation medium described below containing 25 mg/L streptomycin in a 500-mL Sakaguchi flask, followed by culturing at 37° C. for 48 hours using a reciprocal shaker.

The composition of the medium used for the L-lysine fermentation is shown below. Sodium oleate, or a mixture of sodium oleate and sodium palmitate was dissolved into the fermentation medium as the carbon source, without any surfactant. The following ingredients were also present in the medium: poly(oxyethylene) sorbitan monooleate (Tween 80), n-octyl β-D-glucoside (Octyl Glucoside: Nacalai Tesque, Inc.) serving as an alkyl glucoside, or N,N-dimethyl-N-dodecylglycine betaine (product name EMPIGEN BB: Fluka) serving as zwitterionic surfactant. The total content of the carbon source in each medium was adjusted to 20 g/L.

*Escherichia* Bacterium L-Lysine Fermentation Medium:

| Carbon source | 20 g/L |
|---|---|
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.01 g/L |
| Yeast extract | 2.0 g/L |
| $CaCO_3$ (Japanese Pharmacopoeia) | 30 g/L |

The medium was adjusted to pH 7.0 with KOH and sterilized in an autoclave at 120° C. for 20 minutes. The carbon source and $MgSO_4 \cdot 7H_2O$ were separately sterilized and mixed. $CaCO_3$ was added after dry heat sterilization.

After 24 hours and 48 hours, the amount of L-lysine in the culture supernatants was determined using a bioanalyzer AS210 (Sakura Finetechnical Co., Ltd.). Growth could not be determined based on the turbidities (ODs), and therefore, culture media diluted to appropriate concentrations were applied onto LB plates, followed by determination of the number of viable cells. The results are shown in Table 4 as the mean of duplicate culture.

Whether using oleic acid alone, or a mixture of equal amounts of palmitic acid and oleic acid, as the carbon source, addition of Tween 80, Octyl-Glucoside, and EMPIGEN BB together increased the L-lysine production amount compared with when surfactant was not added.

TABLE 4

Results of culture of the L-lysine-producing strain using fatty acid added with various surfactants

| Carbon source | Additive (0.5%) | Culture time (h) | Viable cells ($10^8$/ml) | L-lysine (g/l) |
|---|---|---|---|---|
| Oleic acid 20 g/l | None | 24 | 12.1 | 1.9 |
| | | 48 | 5.6 | 1.9 |
| Oleic acid 20 g/l | Tween 80 | 24 | 10.6 | 2.7 |
| | | 48 | 1.7 | 3.2 |
| Oleic acid 20 g/l | Octyl-Glucoside | 24 | 9.5 | 2.2 |
| | | 48 | 0 | 2.9 |
| Oleic acid 20 g/l | EMPIGEN BB | 24 | 13.3 | 2.2 |
| | | 48 | 2.9 | 2.8 |
| Palmitic acid 10 g/l + Oleic acid 10 g/l | None | 24 | 3.6 | 2.7 |
| | | 48 | 8.0 | 3.0 |
| Palmitic acid 10 g/l + Oleic acid 10 g/l | Tween 80 | 24 | 7.8 | 2.9 |
| | | 48 | 15.1 | 3.5 |
| Palmitic acid 10 g/l + Oleic acid 10 g/l | Octyl-Glucoside | 24 | 2.4 | 2.9 |
| | | 48 | 0.0 | 3.6 |
| Palmitic acid 10 g/l + Oleic acid 10 g/l | EMPIGEN BB | 24 | 6.4 | 3.1 |
| | | 48 | 2.0 | 3.8 |

Example 6

Culture of the L-Lysine-Producing Strain of *Escherichia* Bacterium Using a Mixture of Fatty Acids The glycerol stock of WC196LC/pCABD2 strain was thawed, and 100 µL of the stock was uniformly applied onto an L-plate containing 25 mg/L streptomycin, and the cells were cultured at 37° C. for 24 hours. About one-eighth of the cells on the plate were inoculated into 20 mL of the fermentation medium described below containing 25 mg/L streptomycin in a 500-mL Sakaguchi flask, followed by culturing at 37° C. for 48 hours using a reciprocal shaker.

The composition of the medium used for the L-lysine fermentation is shown below. Mixtures having different ratios of sodium palmitate to sodium oleate were dissolved into the fermentation medium as the carbon source with 0.5% of poly(oxyethylene) sorbitan monooleate (Tween 80) (manufactured by Nacalai Tesque, Inc.). The total content of the carbon source in each medium was adjusted to 20 g/L.

*Escherichia* Bacterium L-Lysine Fermentation Medium:

| | |
|---|---|
| Carbon source | 20 g/L |
| Tween 80 | 5.0 g/L |
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.01 g/L |
| Yeast extract | 2.0 g/L |
| $CaCO_3$ (Japanese Pharmacopoeia) | 30 g/L |

The medium was adjusted to pH 7.0 with KOH and sterilized in an autoclave at 120° C. for 20 minutes. The carbon source and $MgSO_4 \cdot 7H_2O$ were separately sterilized and mixed. $CaCO_3$ was added after dry heat sterilization.

After 24 and 48 hours, the amount of L-lysine in the culture supernatants was determined using a bioanalyzer AS210 (Sakura Finetechnical Co., Ltd.). Growth could not be determined based on the turbidities (ODs), and therefore, culture media diluted to appropriate concentrations were applied onto LB plates, followed by determination of the number of viable cells. The results are shown in Table 5 as the mean of duplicate cultures.

It was found that an increase in the ratio of palmitic acid to oleic acid led to an increase in the level of accumulated L-lysine. However, when using the mixture of oleic acid and palmitic acid at the ratio of 1:1.5, the level of accumulated L-lysine decreased. These results revealed that the appropriate mixing ratio of oleic acid to palmitic acid suitable for L-lysine production was 1:1.22.

TABLE 5

Results of culture of the L-lysine-producing strain using the mixture of oleic acid and palmitic acid with different mixing ratios

| Carbon source | Culture time (h) | Viable cells ($10^8$/ml) | L-lysine (g/l) |
|---|---|---|---|
| Palmitic acid 2 g/l + | 24 | 3.4 | 2.1 |
| Oleic acid 18 g/l | 48 | 20.0 | 2.3 |
| Palmitic acid 6.7 g/l + | 24 | 3.0 | 2.5 |
| Oleic acid 13.3 g/l | 48 | 41.1 | 2.7 |
| Palmitic acid 10 g/l + | 24 | 7.4 | 2.7 |
| Oleic acid 10 g/l | 48 | 21.2 | 3.1 |
| Palmitic acid 11 g/l + | 24 | 4.2 | 2.7 |
| Oleic acid 9 g/l | 48 | 2.6 | 3.1 |
| Palmitic acid 12 g/l + | 24 | 0.03 | 0.2 |
| Oleic acid 8 g/l | 48 | 0.26 | 0.2 |

Example 7

Culture of the L-Threonine-Producing Strain of *Escherichia* Bacterium Using Various Fatty Acids

*Escherichia coli* B-5318, an L-threonine-producing bacterium, was cultured on LB agar medium (10 g/L tryptone, 5 g/L yeast extract, 10 g/L NaCl, 15 g/L agar) containing 20 mg/L of streptomycin sulfate at 37° C. for 24 hours. The cells on the agar medium were scraped off and inoculated into a 500-ml baffle flask containing 20 mL of the fermentation medium shown below, followed by culturing at the temperature of 40° C. for 48 hours.

The composition of the medium used for the L-threonine fermentation is shown below. Each of the fatty acids was dissolved into water at the concentration of 20 g/L at about 80° C., and for linoleic acid, the mixture of linoleic acid and water was adjusted to be pH 10.5 with 3N NaOH. Then, Tween 80, which was sterilized with a filter (pore size 0.2 µm), was added to each fatty acid solution to a final concentration of 1.0%, and the obtained solutions containing each fatty acid were emulsified with homogenizer (PT3100: Polytron) at 10,000 rpm for 10 minutes. Then, the solutions were adjusted to pH 7.0, followed by autoclaving at 110° C. for 10 minutes. These solutions were used as the carbon source below.

*Escherichia* Bacterium L-Threonine Fermentation Medium:

| | |
|---|---|
| Carbon source | 10 g/L |
| Tween 80 | 5.0 g/L |
| $(NH_4)_2SO_4$ | 16 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.01 g/L |
| Yeast extract | 2.0 g/L |
| PIPES (pH7.0) | 20 g/L |

The medium was adjusted to pH 7.0 with KOH and sterilized in an autoclave at 110° C. for 10 minutes. The carbon source and PIPES (pH7.0) were separately sterilized and mixed.

After 48 hours, the culture supernatants were analyzed by liquid chromatography to determine the amount of L-threonine. To evaluate growth, an equal amount of 10% Tween 80 solution was added to the culture, and optical density ($OD_{600}$) was measured. The results are shown in Table 6 as the mean of duplicate cultures.

L-threonine production was observed whether using myristic acid, palmitic acid, stearic acid, oleic acid or linoleic acid as the carbon source, and the amount of L-lysine produced was particularly high when using myristic acid, palmitic acid, stearic acid, or oleic acid.

TABLE 6

L-threonine production using various fatty acids

| Fatty acid (10 g/L) | Culture time (h) | OD$_{600}$ | L-threonine (g/L) |
|---|---|---|---|
| Myristic acid | 48 | 1.1 | 0.5 |
| Palmitic acid | 48 | 3.4 | 2.3 |
| Stearic acid | 48 | 4.5 | 3.5 |
| Oleic acid | 48 | 3.6 | 3.6 |
| Linoleic acid | 48 | 2.7 | 0.7 |

Example 8

Culture of the L-Lysine-Producing Strain of Escherichia Bacterium Using Various Fatty Acids The glycerol stock of WC196LC/pCABD2 strain was thawed, and 50 µL of the stock was uniformly applied onto an L-plate containing 25 mg/L streptomycin, and the cells were cultured at 37° C. for 24 hours. About one-fourth of the cells on the plate were inoculated into 20 mL of the fermentation medium described below containing 25 mg/L streptomycin in a 500-mL baffled flask, followed by culturing at 37° C. for 48 hours using a reciprocal shaker.

The composition of the medium used for the L-lysine fermentation is shown below. Each of the fatty acids was dissolved in water to a concentration of 20 g/L at about 80° C., and for linoleic acid, the mixture of linoleic acid and water was adjusted to be pH 10.5 with 3N NaOH. Then, Tween 80, which was sterilized with a filter (pore size 0.2 µm), was added to each fatty acid solution to a final concentration of 1.0%, and the obtained solutions containing each fatty acid were emulsified with homogenizer (PT3100: Polytron) at 10,000 rpm for 10 minutes. Then, the solutions were adjusted to pH 7.0, followed by autoclaving at 110° C. for 10 minutes. These solutions were used as the carbon source below. For control, glucose was added as the carbon source.

Escherichia Bacterium L-Lysine-Producing Medium:

| | |
|---|---|
| Carbon source (fatty acid or glucose) | 10 g/L |
| Tween 80 (added to fatty acid) | 5.0 g/L |
| (NH$_4$)$_2$SO$_4$ | 24 g/L |
| KH$_2$PO$_4$ | 1.0 g/L |
| MgSO$_4$•7H$_2$O | 1.0 g/L |
| FeSO$_4$•7H$_2$O | 0.01 g/L |
| MnSO$_4$•7H$_2$O | 0.01 g/L |
| Yeast extract | 2.0 g/L |
| PIPES (pH7.0) | 20 g/L |

The medium was adjusted to pH 7.0 with KOH and sterilized in an autoclave at 110° C. for 10 minutes. The carbon source and PIPES (pH7.0) were separately sterilized and mixed.

After 48 hours, the amount of L-lysine in the culture supernatants was determined using a bioanalyzer AS210 (Sakura Finetechnical Co., Ltd.). To evaluate growth, an equal amount of 10% Tween 80 solution was added to the culture, and optical density (OD$_{600}$) was measured. The results are shown in Table 7 as the mean of duplicate cultures.

L-lysine production was observed whether using myristic acid, palmitic acid, stearic acid, oleic acid, or linoleic acid as the carbon source, and the amount of L-lysine produced was particularly high when using myristic acid, palmitic acid, stearic acid, or oleic acid, which was comparable to the amount when using glucose as the carbon source.

TABLE 7

L-lysine production using various fatty acids

| Fatty acid (10 g/L) | Culture time (h) | OD$_{600}$ | L-lysine (g/L) |
|---|---|---|---|
| Mylistic acid | 48 | 3.7 | 2.5 |
| Palmitic acid | 48 | 6.5 | 3.9 |
| Stearic acid | 48 | 7.2 | 4.0 |
| Oleic acid | 48 | 6.2 | 3.2 |
| Linoleic acid | 48 | 1.1 | 0.5 |
| Glucose | 48 | 3.5 | 4.2 |

Description of Sequence Listing:

SEQ ID NO. 1: PCR primer for cadA gene disruption
SEQ ID NO. 2: PCR primer for cadA gene disruption
SEQ ID NO. 3: PCR primer for ldcC gene disruption
SEQ ID NO. 4: PCR primer for ldcC gene disruption
SEQ ID NO. 5: Nucleotide sequence of cadA gene
SEQ ID NO. 6: Amino acid sequence encoded by cadA gene
SEQ ID NO. 7: Nucleotide sequence of ldcC gene
SEQ ID NO. 8: Amino acid sequence encoded by ldcC gene Industrial Applicability In accordance with the presently disclosed subject matter, L-amino acids are produced at low cost by using fatty acids as an inexpensive carbon source.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid, comprising culturing a bacterium of the Enterobacteriaceae family having an L-amino acid-producing ability in a medium containing an emulsified fatty acid as a carbon source under conditions suitable to produce said L-amino acid, and collecting the L-amino acid from the medium or bacterium, wherein said fatty acid is emulsified by homogenization and/or ultrasonication in the presence of a surfactant under alkali conditions.

2. The method according to claim 1, wherein said fatty acid is a fatty acid having no less than 14 carbons.

3. The method according to claim 1, wherein said fatty acid is selected from the group consisting of myristic acid, palmitic acid, stearic acid, oleic acid, linoleic acid, and combinations thereof.

4. The method according to claim 1, wherein said medium comprises said fatty acid in an amount of 0.2 to 10 w/v %.

5. The method according to claim 1, wherein said medium further comprises a carbon source other than a fatty acid.

6. The method according to claim 1, wherein said bacterium belongs to the genus *Escherichia*.

7. The method according to claim 1, wherein said L-amino acid is selected from the group consisting of L-threonine, L-lysine, L-phenylalanine, L-tryptophan, L-valine, L-leucine, L-isoleucine, L-methionine, and combinations thereof.

8. The method according to claim 1, wherein the L-amino acid is selected from the group consisting of L-threonine, L-lysine, and combinations thereof.

9. The method according to claim 1, wherein said bacterium is *Escherichia coli*.

10. The method according to claim 1, wherein said alkali conditions comprise pH 9 or more.

11. The method according to claim 5, wherein the carbon source other than a fatty acid is glucose.

\* \* \* \* \*

SEQUENCE LISTING

```
<160> NUMBER OF SEQ ID NOS: 8

<210> SEQ ID NO 1
<211> LENGTH: 54
<212> TYPE: DNA
<213> ORGANISM: Artificial sequence
<220> FEATURE:
<223> OTHER INFORMATION: 5'-primer for cadA

<400> SEQUENCE: 1
tttgctttct tctttcaata ccttaacggt atagcgtgaa gcctgctttt ttat          54

<210> SEQ ID NO 2
```

```
<211> LENGTH: 54
<212> TYPE: DNA
<213> ORGANISM: Artificial sequence
<220> FEATURE:
<223> OTHER INFORMATION: 3'-primer for cadA

<400> SEQUENCE: 2
agatatgact atgaacgtta ttgcaatatt gaatcacgct caagttagta taaa           54

<210> SEQ ID NO 3
<211> LENGTH: 54
<212> TYPE: DNA
<213> ORGANISM: Artificial sequence
<220> FEATURE:
<223> OTHER INFORMATION: 5'-primer for ldcC

<400> SEQUENCE: 3
ggaggaacac atgaacatca ttgccattat gggacctgaa gcctgctttt ttat           54

<210> SEQ ID NO 4
<211> LENGTH: 53
<212> TYPE: DNA
<213> ORGANISM: Artificial sequence
<220> FEATURE:
<223> OTHER INFORMATION: 3'-primer for ldcC

<400> SEQUENCE: 4
cgccattttt aggactcgta cgcggtaaac gccgtccgtc aagttagtat aaa            53

<210> SEQ ID NO 5
<211> LENGTH: 2148
<212> TYPE: DNA
<213> ORGANISM: Escherichia coli
<220> FEATURE:
<221> NAME/KEY: CDS
<222> LOCATION: (1)..(2145)

<400> SEQUENCE: 5
```

| | | | | | | | | | | | | | | | | |
|---|---|---|---|---|---|---|---|---|---|---|---|---|---|---|---|---|
| atg | aac | gtt | att | gca | ata | ttg | aat | cac | atg | ggg | gtt | tat | ttt | aaa | gaa | 48 |
| Met | Asn | Val | Ile | Ala | Ile | Leu | Asn | His | Met | Gly | Val | Tyr | Phe | Lys | Glu | |
| 1 | | | | 5 | | | | | 10 | | | | | 15 | | |
| gaa | ccc | atc | cgt | gaa | ctt | cat | cgc | gcg | ctt | gaa | cgt | ctg | aac | ttc | cag | 96 |
| Glu | Pro | Ile | Arg | Glu | Leu | His | Arg | Ala | Leu | Glu | Arg | Leu | Asn | Phe | Gln | |
| | | | 20 | | | | | 25 | | | | | 30 | | | |
| att | gtt | tac | ccg | aac | gac | cgt | gac | gac | tta | tta | aaa | ctg | atc | gaa | aac | 144 |
| Ile | Val | Tyr | Pro | Asn | Asp | Arg | Asp | Asp | Leu | Leu | Lys | Leu | Ile | Glu | Asn | |
| | | | 35 | | | | | 40 | | | | | 45 | | | |
| aat | gcg | cgt | ctg | tgc | ggc | gtt | att | ttt | gac | tgg | gat | aaa | tat | aat | ctc | 192 |
| Asn | Ala | Arg | Leu | Cys | Gly | Val | Ile | Phe | Asp | Trp | Asp | Lys | Tyr | Asn | Leu | |
| | 50 | | | | | 55 | | | | | 60 | | | | | |
| gag | ctg | tgc | gaa | gaa | att | agc | aaa | atg | aac | gag | aac | ctg | ccg | ttg | tac | 240 |
| Glu | Leu | Cys | Glu | Glu | Ile | Ser | Lys | Met | Asn | Glu | Asn | Leu | Pro | Leu | Tyr | |
| 65 | | | | | 70 | | | | | 75 | | | | | 80 | |
| gcg | ttc | gct | aat | acg | tat | tcc | act | ctc | gat | gta | agc | ctg | aat | gac | ctg | 288 |
| Ala | Phe | Ala | Asn | Thr | Tyr | Ser | Thr | Leu | Asp | Val | Ser | Leu | Asn | Asp | Leu | |
| | | | | 85 | | | | | 90 | | | | | 95 | | |
| cgt | tta | cag | att | agc | ttc | ttt | gaa | tat | gcg | ctg | ggt | gct | gct | gaa | gat | 336 |
| Arg | Leu | Gln | Ile | Ser | Phe | Phe | Glu | Tyr | Ala | Leu | Gly | Ala | Ala | Glu | Asp | |
| | | | 100 | | | | | 105 | | | | | 110 | | | |
| att | gct | aat | aag | atc | aag | cag | acc | act | gac | gaa | tat | atc | aac | act | att | 384 |
| Ile | Ala | Asn | Lys | Ile | Lys | Gln | Thr | Thr | Asp | Glu | Tyr | Ile | Asn | Thr | Ile | |
| | | | 115 | | | | | 120 | | | | | 125 | | | |
| ctg | cct | ccg | ctg | act | aaa | gca | ctg | ttt | aaa | tat | gtt | cgt | gaa | ggt | aaa | 432 |
| Leu | Pro | Pro | Leu | Thr | Lys | Ala | Leu | Phe | Lys | Tyr | Val | Arg | Glu | Gly | Lys | |
| | | 130 | | | | | 135 | | | | | 140 | | | | |

-continued

| | | |
|---|---|---|
| tat act ttc tgt act cct ggt cac atg ggc ggt act gca ttc cag aaa<br>Tyr Thr Phe Cys Thr Pro Gly His Met Gly Gly Thr Ala Phe Gln Lys<br>145                          150                          155                          160 | 480 |
| agc ccg gta ggt agc ctg ttc tat gat ttc ttt ggt ccg aat acc atg<br>Ser Pro Val Gly Ser Leu Phe Tyr Asp Phe Phe Gly Pro Asn Thr Met<br>                165                        170                        175 | 528 |
| aaa tct gat att tcc att tca gta tct gaa ctg ggt tct ctg ctg gat<br>Lys Ser Asp Ile Ser Ile Ser Val Ser Glu Leu Gly Ser Leu Leu Asp<br>                180                        185                        190 | 576 |
| cac agt ggt cca cac aaa gaa gca gaa cag tat atc gct cgc gtc ttt<br>His Ser Gly Pro His Lys Glu Ala Glu Gln Tyr Ile Ala Arg Val Phe<br>           195                        200                        205 | 624 |
| aac gca gac cgc agc tac atg gtg acc aac ggt act tcc act gcg aac<br>Asn Ala Asp Arg Ser Tyr Met Val Thr Asn Gly Thr Ser Thr Ala Asn<br>210                          215                        220 | 672 |
| aaa att gtt ggt atg tac tct gct cca gca ggc agc acc att ctg att<br>Lys Ile Val Gly Met Tyr Ser Ala Pro Ala Gly Ser Thr Ile Leu Ile<br>225                          230                        235                        240 | 720 |
| gac cgt aac tgc cac aaa tcg ctg acc cac ctg atg atg agc gat<br>Asp Arg Asn Cys His Lys Ser Leu Thr His Leu Met Met Met Ser Asp<br>                    245                        250                        255 | 768 |
| gtt acg cca atc tat ttc cgc ccg acc cgt aac gct tac ggt att ctt<br>Val Thr Pro Ile Tyr Phe Arg Pro Thr Arg Asn Ala Tyr Gly Ile Leu<br>                260                        265                        270 | 816 |
| ggt ggt atc cca cag agt gaa ttc cag cac gct acc att gct aag cgc<br>Gly Gly Ile Pro Gln Ser Glu Phe Gln His Ala Thr Ile Ala Lys Arg<br>           275                        280                        285 | 864 |
| gtg aaa gaa aca cca aac gca acc tgg ccg gta cat gct gta att acc<br>Val Lys Glu Thr Pro Asn Ala Thr Trp Pro Val His Ala Val Ile Thr<br>290                          295                        300 | 912 |
| aac tct acc tat gat ggt ctg ctg tac aac acc gac ttc atc aag aaa<br>Asn Ser Thr Tyr Asp Gly Leu Leu Tyr Asn Thr Asp Phe Ile Lys Lys<br>305                          310                        315                        320 | 960 |
| aca ctg gat gtg aaa tcc atc cac ttt gac tcc gcg tgg gtg cct tac<br>Thr Leu Asp Val Lys Ser Ile His Phe Asp Ser Ala Trp Val Pro Tyr<br>                     325                        330                        335 | 1008 |
| acc aac ttc tca ccg att tac gaa ggt aaa tgc ggt atg agc ggt ggc<br>Thr Asn Phe Ser Pro Ile Tyr Glu Gly Lys Cys Gly Met Ser Gly Gly<br>                340                        345                        350 | 1056 |
| cgt gta gaa ggg aaa gtg att tac gaa acc cag tcc act cac aaa ctg<br>Arg Val Glu Gly Lys Val Ile Tyr Glu Thr Gln Ser Thr His Lys Leu<br>           355                        360                        365 | 1104 |
| ctg gcg gcg ttc tct cag gct tcc atg atc cac gtt aaa ggt gac gta<br>Leu Ala Ala Phe Ser Gln Ala Ser Met Ile His Val Lys Gly Asp Val<br>370                          375                        380 | 1152 |
| aac gaa gaa acc ttt aac gaa gcc tac atg atg cac acc acc act tct<br>Asn Glu Glu Thr Phe Asn Glu Ala Tyr Met Met His Thr Thr Thr Ser<br>385                          390                        395                        400 | 1200 |
| ccg cac tac ggt atc gtg gcg tcc act gaa acc gct gcg gcg atg atg<br>Pro His Tyr Gly Ile Val Ala Ser Thr Glu Thr Ala Ala Ala Met Met<br>                    405                        410                        415 | 1248 |
| aaa ggc aat gca ggt aag cgt ctg atc aac ggt tct att gaa cgt gcg<br>Lys Gly Asn Ala Gly Lys Arg Leu Ile Asn Gly Ser Ile Glu Arg Ala<br>           420                        425                        430 | 1296 |
| atc aaa ttc cgt aaa gag atc aaa cgt ctg aga acg gaa tct gat ggc<br>Ile Lys Phe Arg Lys Glu Ile Lys Arg Leu Arg Thr Glu Ser Asp Gly<br>435                          440                        445 | 1344 |
| tgg ttc ttt gat gta tgg cag ccg gat cat atc gat acg act gaa tgc<br>Trp Phe Phe Asp Val Trp Gln Pro Asp His Ile Asp Thr Thr Glu Cys<br>450                          455                        460 | 1392 |

```
tgg ccg ctg cgt tct gac agc acc tgg cac ggc ttc aaa aac atc gat   1440
Trp Pro Leu Arg Ser Asp Ser Thr Trp His Gly Phe Lys Asn Ile Asp
465                 470                 475                 480 aac gag cac atg tat ctt gac ccg atc aaa gtc acc ctg ctg act ccg   1488
Asn Glu His Met Tyr Leu Asp Pro Ile Lys Val Thr Leu Leu Thr Pro
                485                 490                 495 ggg atg gaa aaa gac ggc acc atg agc gac ttt ggt att ccg gcc agc   1536
Gly Met Glu Lys Asp Gly Thr Met Ser Asp Phe Gly Ile Pro Ala Ser
            500                 505                 510 atc gtg gcg aaa tac ctc gac gaa cat ggc atc gtt gtt gag aaa acc   1584
Ile Val Ala Lys Tyr Leu Asp Glu His Gly Ile Val Val Glu Lys Thr
        515                 520                 525 ggt ccg tat aac ctg ctg ttc ctg ttc agc atc ggt atc gat aag acc   1632
Gly Pro Tyr Asn Leu Leu Phe Leu Phe Ser Ile Gly Ile Asp Lys Thr
    530                 535                 540 aaa gca ctg agc ctg ctg cgt gct ctg act gac ttt aaa cgt gcg ttc   1680
Lys Ala Leu Ser Leu Leu Arg Ala Leu Thr Asp Phe Lys Arg Ala Phe
545                 550                 555                 560 gac ctg aac ctg cgt gtg aaa aac atg ctg ccg tct ctg tat cgt gaa   1728
Asp Leu Asn Leu Arg Val Lys Asn Met Leu Pro Ser Leu Tyr Arg Glu
                565                 570                 575 gat cct gaa ttc tat gaa aac atg cgt att cag gaa ctg gct cag aat   1776
Asp Pro Glu Phe Tyr Glu Asn Met Arg Ile Gln Glu Leu Ala Gln Asn
            580                 585                 590 atc cac aaa ctg att gtt cac cac aat ctg ccg gat ctg atg tat cgc   1824
Ile His Lys Leu Ile Val His His Asn Leu Pro Asp Leu Met Tyr Arg
        595                 600                 605 gca ttt gaa gtg ctg ccg acg atg gta atg act ccg tat gct gca ttc   1872
Ala Phe Glu Val Leu Pro Thr Met Val Met Thr Pro Tyr Ala Ala Phe
    610                 615                 620 cag aaa gag ctg cac ggt atg acc gaa gaa gtt tac ctc gac gaa atg   1920
Gln Lys Glu Leu His Gly Met Thr Glu Glu Val Tyr Leu Asp Glu Met
625                 630                 635                 640 gta ggt cgt att aac gcc aat atg atc ctt ccg tac ccg ccg gga gtt   1968
Val Gly Arg Ile Asn Ala Asn Met Ile Leu Pro Tyr Pro Pro Gly Val
                645                 650                 655 cct ctg gta atg ccg ggt gaa atg atc acc gaa gaa agc cgt ccg gtt   2016
Pro Leu Val Met Pro Gly Glu Met Ile Thr Glu Glu Ser Arg Pro Val
            660                 665                 670 ctg gag ttc ctg cag atg ctg tgt gaa atc ggc gct cac tat ccg ggc   2064
Leu Glu Phe Leu Gln Met Leu Cys Glu Ile Gly Ala His Tyr Pro Gly
        675                 680                 685 ttt gaa acc gat att cac ggt gca tac cgt cag gct gat ggc cgc tat   2112
Phe Glu Thr Asp Ile His Gly Ala Tyr Arg Gln Ala Asp Gly Arg Tyr
    690                 695                 700 acc gtt aag gta ttg aaa gaa gaa agc aaa aaa taa                   2148
Thr Val Lys Val Leu Lys Glu Glu Ser Lys Lys
705                 710                 715

<210> SEQ ID NO 6
<211> LENGTH: 715
<212> TYPE: PRT
<213> ORGANISM: Escherichia coli

<400> SEQUENCE: 6

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
```

```
                    35                  40                  45
Asn Ala Arg Leu Cys Gly Val Ile Phe Asp Trp Asp Lys Tyr Asn Leu
 50                  55                  60
Glu Leu Cys Glu Glu Ile Ser Lys Met Asn Glu Asn Leu Pro Leu Tyr
 65                  70                  75                  80
Ala Phe Ala Asn Thr Tyr Ser Thr Leu Asp Val Ser Leu Asn Asp Leu
                     85                  90                  95
Arg Leu Gln Ile Ser Phe Phe Glu Tyr Ala Leu Gly Ala Ala Glu Asp
                    100                 105                 110
Ile Ala Asn Lys Ile Lys Gln Thr Thr Asp Glu Tyr Ile Asn Thr Ile
                    115                 120                 125
Leu Pro Pro Leu Thr Lys Ala Leu Phe Lys Tyr Val Arg Glu Gly Lys
                    130                 135                 140
Tyr Thr Phe Cys Thr Pro Gly His Met Gly Gly Thr Ala Phe Gln Lys
145                 150                 155                 160
Ser Pro Val Gly Ser Leu Phe Tyr Asp Phe Phe Gly Pro Asn Thr Met
                    165                 170                 175
Lys Ser Asp Ile Ser Ile Ser Val Ser Glu Leu Gly Ser Leu Leu Asp
                    180                 185                 190
His Ser Gly Pro His Lys Glu Ala Glu Gln Tyr Ile Ala Arg Val Phe
                    195                 200                 205
Asn Ala Asp Arg Ser Tyr Met Val Thr Asn Gly Thr Ser Thr Ala Asn
                    210                 215                 220
Lys Ile Val Gly Met Tyr Ser Ala Pro Ala Gly Ser Thr Ile Leu Ile
225                 230                 235                 240
Asp Arg Asn Cys His Lys Ser Leu Thr His Leu Met Met Met Ser Asp
                    245                 250                 255
Val Thr Pro Ile Tyr Phe Arg Pro Thr Arg Asn Ala Tyr Gly Ile Leu
                    260                 265                 270
Gly Gly Ile Pro Gln Ser Glu Phe Gln His Ala Thr Ile Ala Lys Arg
                    275                 280                 285
Val Lys Glu Thr Pro Asn Ala Thr Trp Pro Val His Ala Val Ile Thr
                    290                 295                 300
Asn Ser Thr Tyr Asp Gly Leu Leu Tyr Asn Thr Asp Phe Ile Lys Lys
305                 310                 315                 320
Thr Leu Asp Val Lys Ser Ile His Phe Asp Ser Ala Trp Val Pro Tyr
                    325                 330                 335
Thr Asn Phe Ser Pro Ile Tyr Glu Gly Lys Cys Gly Met Ser Gly Gly
                    340                 345                 350
Arg Val Glu Gly Lys Val Ile Tyr Glu Thr Gln Ser Thr His Lys Leu
                    355                 360                 365
Leu Ala Ala Phe Ser Gln Ala Ser Met Ile His Val Lys Gly Asp Val
                    370                 375                 380
Asn Glu Glu Thr Phe Asn Glu Ala Tyr Met Met His Thr Thr Thr Ser
385                 390                 395                 400
Pro His Tyr Gly Ile Val Ala Ser Thr Glu Thr Ala Ala Ala Met Met
                    405                 410                 415
Lys Gly Asn Ala Gly Lys Arg Leu Ile Asn Gly Ser Ile Glu Arg Ala
                    420                 425                 430
Ile Lys Phe Arg Lys Glu Ile Lys Arg Leu Arg Thr Glu Ser Asp Gly
                    435                 440                 445
Trp Phe Phe Asp Val Trp Gln Pro Asp His Ile Asp Thr Thr Glu Cys
                    450                 455                 460
```

```
Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
            485                 490                 495

Gly Met Glu Lys Asp Gly Thr Met Ser Asp Phe Gly Ile Pro Ala Ser
        500                 505                 510

Ile Val Ala Lys Tyr Leu Asp Glu His Gly Ile Val Val Glu Lys Thr
    515                 520                 525

Gly Pro Tyr Asn Leu Leu Phe Leu Phe Ser Ile Gly Ile Asp Lys Thr
530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 7
<211> LENGTH: 2142
<212> TYPE: DNA
<213> ORGANISM: Escherichia coli
<220> FEATURE:
<221> NAME/KEY: CDS
<222> LOCATION: (1)..(2139)

<400> SEQUENCE: 7 atg aac atc att gcc att atg gga ccg cat ggc gtc ttt tat aaa gat    48
Met Asn Ile Ile Ala Ile Met Gly Pro His Gly Val Phe Tyr Lys Asp
1               5                   10                  15 gag ccc atc aaa gaa ctg gag tcg gcg ctg gtg gcg caa ggc ttt cag    96
Glu Pro Ile Lys Glu Leu Glu Ser Ala Leu Val Ala Gln Gly Phe Gln
            20                  25                  30 att atc tgg cca caa aac agc gtt gat ttg ctg aaa ttt atc gag cat   144
Ile Ile Trp Pro Gln Asn Ser Val Asp Leu Leu Lys Phe Ile Glu His
        35                  40                  45 aac cct cga att tgc ggc gtg att ttt gac tgg gat gag tac agt ctc   192
Asn Pro Arg Ile Cys Gly Val Ile Phe Asp Trp Asp Glu Tyr Ser Leu
    50                  55                  60 gat tta tgt agc gat atc aat cag ctt aat gaa tat ctc ccg ctt tat   240
Asp Leu Cys Ser Asp Ile Asn Gln Leu Asn Glu Tyr Leu Pro Leu Tyr
65                  70                  75                  80 gcc ttc atc aac acc cac tcg acg atg gat gtc agc gtg cag gat atg   288
```

-continued

```
                Ala Phe Ile Asn Thr His Ser Thr Met Asp Val Ser Val Gln Asp Met
                                85                  90                  95 cgg atg gcg ctc tgg ttt ttt gaa tat gcg ctg ggg cag gcg gaa gat        336
Arg Met Ala Leu Trp Phe Phe Glu Tyr Ala Leu Gly Gln Ala Glu Asp
            100                 105                 110 atc gcc att cgt atg cgt cag tac acc gac gaa tat ctt gat aac att        384
Ile Ala Ile Arg Met Arg Gln Tyr Thr Asp Glu Tyr Leu Asp Asn Ile
            115                 120                 125 aca ccg ccg ttc acg aaa gcc ttg ttt acc tac gtc aaa gag cgg aag        432
Thr Pro Pro Phe Thr Lys Ala Leu Phe Thr Tyr Val Lys Glu Arg Lys
            130                 135                 140 tac acc ttt tgt acg ccg ggg cat atg ggc ggc acc gca tat caa aaa        480
Tyr Thr Phe Cys Thr Pro Gly His Met Gly Gly Thr Ala Tyr Gln Lys
145                 150                 155                 160 agc ccg gtt ggc tgt ctg ttt tat gat ttt ttc ggc ggg aat act ctt        528
Ser Pro Val Gly Cys Leu Phe Tyr Asp Phe Phe Gly Gly Asn Thr Leu
            165                 170                 175 aag gct gat gtc tct att tcg gtc acc gag ctt ggt tcg ttg ctc gac        576
Lys Ala Asp Val Ser Ile Ser Val Thr Glu Leu Gly Ser Leu Leu Asp
            180                 185                 190 cac acc ggg cca cac ctg gaa gcg gaa gag tac atc gcg cgg act ttt        624
His Thr Gly Pro His Leu Glu Ala Glu Glu Tyr Ile Ala Arg Thr Phe
            195                 200                 205 ggc gcg gaa cag agt tat atc gtt acc aac gga aca tcg acg tcg aac        672
Gly Ala Glu Gln Ser Tyr Ile Val Thr Asn Gly Thr Ser Thr Ser Asn
            210                 215                 220 aaa att gtg ggt atg tac gcc gcg cca tcc ggc agt acg ctg ttg atc        720
Lys Ile Val Gly Met Tyr Ala Ala Pro Ser Gly Ser Thr Leu Leu Ile
225                 230                 235                 240 gac cgc aat tgt cat aaa tcg ctg gcg cat ctg ttg atg atg aac gat        768
Asp Arg Asn Cys His Lys Ser Leu Ala His Leu Leu Met Met Asn Asp
            245                 250                 255 gta gtg cca gtc tgg ctg aaa ccg acg cgt aat gcg ttg ggg att ctt        816
Val Val Pro Val Trp Leu Lys Pro Thr Arg Asn Ala Leu Gly Ile Leu
            260                 265                 270 ggt ggg atc ccg cgc cgt gaa ttt act cgc gac agc atc gaa gag aaa        864
Gly Gly Ile Pro Arg Arg Glu Phe Thr Arg Asp Ser Ile Glu Glu Lys
            275                 280                 285 gtc gct gct acc acg caa gca caa tgg ccg gtt cat gcg gtg atc acc        912
Val Ala Ala Thr Thr Gln Ala Gln Trp Pro Val His Ala Val Ile Thr
            290                 295                 300 aac tcc acc tat gat ggc ttg ctc tac aac acc gac tgg atc aaa cag        960
Asn Ser Thr Tyr Asp Gly Leu Leu Tyr Asn Thr Asp Trp Ile Lys Gln
305                 310                 315                 320 acg ctg gat gtc ccg tcg att cac ttc gat tct gcc tgg gtg ccg tac       1008
Thr Leu Asp Val Pro Ser Ile His Phe Asp Ser Ala Trp Val Pro Tyr
            325                 330                 335 acc cat ttt cat ccg atc tac cag ggt aaa agt ggt atg agc ggc gag       1056
Thr His Phe His Pro Ile Tyr Gln Gly Lys Ser Gly Met Ser Gly Glu
            340                 345                 350 cgt gtt gcg gga aaa gtg atc ttc gaa acg caa tcg acc cac aaa atg       1104
Arg Val Ala Gly Lys Val Ile Phe Glu Thr Gln Ser Thr His Lys Met
            355                 360                 365 ctg gcg gcg tta tcg cag gct tcg ctg atc cac att aaa ggc gag tat       1152
Leu Ala Ala Leu Ser Gln Ala Ser Leu Ile His Ile Lys Gly Glu Tyr
            370                 375                 380 gac gaa gag gcc ttt aac gaa gcc ttt atg atg cat acc acc acc tcg       1200
Asp Glu Glu Ala Phe Asn Glu Ala Phe Met Met His Thr Thr Thr Ser
385                 390                 395                 400 ccc agt tat ccc att gtt gct tcg gtt gag acg gcg gcg gcg atg ctg       1248
```

```
Pro Ser Tyr Pro Ile Val Ala Ser Val Glu Thr Ala Ala Ala Met Leu
            405                 410                 415 cgt ggt aat ccg ggc aaa cgg ctg att aac cgt tca gta gaa cga gct      1296
Arg Gly Asn Pro Gly Lys Arg Leu Ile Asn Arg Ser Val Glu Arg Ala
            420                 425                 430 ctg cat ttt cgc aaa gag gtc cag cgg ctg cgg gaa gag tct gac ggt      1344
Leu His Phe Arg Lys Glu Val Gln Arg Leu Arg Glu Glu Ser Asp Gly
            435                 440                 445 tgg ttt ttc gat atc tgg caa ccg ccg cag gtg gat gaa gcc gaa tgc      1392
Trp Phe Phe Asp Ile Trp Gln Pro Pro Gln Val Asp Glu Ala Glu Cys
        450                 455                 460 tgg ccc gtt gcg cct ggc gaa cag tgg cac ggc ttt aac gat gcg gat      1440
Trp Pro Val Ala Pro Gly Glu Gln Trp His Gly Phe Asn Asp Ala Asp
465                 470                 475                 480 gcc gat cat atg ttt ctc gat ccg gtt aaa gtc act att ttg aca ccg      1488
Ala Asp His Met Phe Leu Asp Pro Val Lys Val Thr Ile Leu Thr Pro
                    485                 490                 495 ggg atg gac gag cag ggc aat atg agc gag gag ggg atc ccg gcg gcg      1536
Gly Met Asp Glu Gln Gly Asn Met Ser Glu Glu Gly Ile Pro Ala Ala
            500                 505                 510 ctg gta gca aaa ttc ctc gac gaa cgt ggg atc gta gta gag aaa acc      1584
Leu Val Ala Lys Phe Leu Asp Glu Arg Gly Ile Val Val Glu Lys Thr
            515                 520                 525 ggc cct tat aac ctg ctg ttt ctc ttt agt att ggc atc gat aaa acc      1632
Gly Pro Tyr Asn Leu Leu Phe Leu Phe Ser Ile Gly Ile Asp Lys Thr
530                 535                 540 aaa gca atg gga tta ttg cgt ggg ttg acg gaa ttc aaa cgc tct tac      1680
Lys Ala Met Gly Leu Leu Arg Gly Leu Thr Glu Phe Lys Arg Ser Tyr
545                 550                 555                 560 gat ctc aac ctg cgg atc aaa aat atg cta ccc gat ctc tat gca gaa      1728
Asp Leu Asn Leu Arg Ile Lys Asn Met Leu Pro Asp Leu Tyr Ala Glu
                565                 570                 575 gat ccc gat ttc tac cgc aat atg cgt att cag gat ctg gca caa ggg      1776
Asp Pro Asp Phe Tyr Arg Asn Met Arg Ile Gln Asp Leu Ala Gln Gly
                580                 585                 590 atc cat aag ctg att cgt aaa cac gat ctt ccc ggt ttg atg ttg cgg      1824
Ile His Lys Leu Ile Arg Lys His Asp Leu Pro Gly Leu Met Leu Arg
            595                 600                 605 gca ttc gat act ttg ccg gag atg atc atg acg cca cat cag gca tgg      1872
Ala Phe Asp Thr Leu Pro Glu Met Ile Met Thr Pro His Gln Ala Trp
        610                 615                 620 caa cga caa att aaa ggc gaa gta gaa acc att gcg ctg gaa caa ctg      1920
Gln Arg Gln Ile Lys Gly Glu Val Glu Thr Ile Ala Leu Glu Gln Leu
625                 630                 635                 640 gtc ggt aga gta tcg gca aat atg atc ctg cct tat cca ccg ggc gta      1968
Val Gly Arg Val Ser Ala Asn Met Ile Leu Pro Tyr Pro Pro Gly Val
                645                 650                 655 ccg ctg ttg atg cct gga gaa atg ctg acc aaa gag agc cgc aca gta      2016
Pro Leu Leu Met Pro Gly Glu Met Leu Thr Lys Glu Ser Arg Thr Val
                660                 665                 670 ctc gat ttt cta ctg atg ctt tgt tcc gtc ggg caa cat tac ccc ggt      2064
Leu Asp Phe Leu Leu Met Leu Cys Ser Val Gly Gln His Tyr Pro Gly
            675                 680                 685 ttt gaa acg gat att cac ggc gcg aaa cag gac gaa gac ggt gtt tac      2112
Phe Glu Thr Asp Ile His Gly Ala Lys Gln Asp Glu Asp Gly Val Tyr
        690                 695                 700 cgc gta cga gtc cta aaa atg gcg gga taa                              2142
Arg Val Arg Val Leu Lys Met Ala Gly
705                 710
```

-continued

```
<210> SEQ ID NO 8
<211> LENGTH: 713
<212> TYPE: PRT
<213> ORGANISM: Escherichia coli

<400> SEQUENCE: 8

Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
    50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
        195                 200                 205

Gly Ala Glu Gln Ser Tyr Ile Val Thr Asn Gly Thr Ser Thr Ser Asn
    210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
            260                 265                 270

Gly Gly Ile Pro Arg Arg Glu Phe Thr Arg Asp Ser Ile Glu Glu Lys
        275                 280                 285

Val Ala Ala Thr Thr Gln Ala Gln Trp Pro Val His Ala Val Ile Thr
    290                 295                 300

Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
            340                 345                 350

Arg Val Ala Gly Lys Val Ile Phe Glu Thr Gln Ser Thr His Lys Met
        355                 360                 365

Leu Ala Ala Leu Ser Gln Ala Ser Leu Ile His Ile Lys Gly Glu Tyr
    370                 375                 380

Asp Glu Glu Ala Phe Asn Glu Ala Phe Met Met His Thr Thr Thr Ser
```

-continued

```
            385                 390                 395                 400
Pro Ser Tyr Pro Ile Val Ala Ser Val Glu Thr Ala Ala Ala Met Leu
                405                 410                 415

Arg Gly Asn Pro Gly Lys Arg Leu Ile Asn Arg Ser Val Glu Arg Ala
                420                 425                 430

Leu His Phe Arg Lys Glu Val Gln Arg Leu Arg Glu Glu Ser Asp Gly
                435                 440                 445

Trp Phe Phe Asp Ile Trp Gln Pro Pro Gln Val Asp Glu Ala Glu Cys
                450                 455                 460

Trp Pro Val Ala Pro Gly Glu Gln Trp His Gly Phe Asn Asp Ala Asp
465                 470                 475                 480

Ala Asp His Met Phe Leu Asp Pro Val Lys Val Thr Ile Leu Thr Pro
                485                 490                 495

Gly Met Asp Glu Gln Gly Asn Met Ser Glu Glu Gly Ile Pro Ala Ala
                500                 505                 510

Leu Val Ala Lys Phe Leu Asp Glu Arg Gly Ile Val Val Glu Lys Thr
                515                 520                 525

Gly Pro Tyr Asn Leu Leu Phe Leu Phe Ser Ile Gly Ile Asp Lys Thr
                530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
                565                 570                 575

Asp Pro Asp Phe Tyr Arg Asn Met Arg Ile Gln Asp Leu Ala Gln Gly
                580                 585                 590

Ile His Lys Leu Ile Arg Lys His Asp Leu Pro Gly Leu Met Leu Arg
                595                 600                 605

Ala Phe Asp Thr Leu Pro Glu Met Ile Met Thr Pro His Gln Ala Trp
                610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
                645                 650                 655

Pro Leu Leu Met Pro Gly Glu Met Leu Thr Lys Glu Ser Arg Thr Val
                660                 665                 670

Leu Asp Phe Leu Leu Met Leu Cys Ser Val Gly Gln His Tyr Pro Gly
                675                 680                 685

Phe Glu Thr Asp Ile His Gly Ala Lys Gln Asp Glu Asp Gly Val Tyr
                690                 695                 700

Arg Val Arg Val Leu Lys Met Ala Gly
705                 710
```